(12) United States Patent
Cam et al.

(10) Patent No.: US 10,172,555 B2
(45) Date of Patent: Jan. 8, 2019

(54) DEVICE FOR DETECTING ON-BODY IMPACTS

(71) Applicant: Board of Trustees of the Leland Stanford Junior University, Palo Alto, CA (US)

(72) Inventors: Bruce Cam, Stanford, CA (US); David B. Camarillo, Aptos, CA (US); Lyndia Chun Wu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 170 days.

(21) Appl. No.: 14/199,716

(22) Filed: Mar. 6, 2014

(65) Prior Publication Data

US 2014/0257051 A1    Sep. 11, 2014

Related U.S. Application Data

(60) Provisional application No. 61/775,411, filed on Mar. 8, 2013.

(51) Int. Cl.
*A61B 5/00* (2006.01)
*A61B 5/0205* (2006.01)
(Continued)

(52) U.S. Cl.
CPC ............ *A61B 5/682* (2013.01); *A61B 5/0004* (2013.01); *A61B 5/0205* (2013.01); *A61B 5/1121* (2013.01); *A61B 5/7267* (2013.01); *A61B 5/7282* (2013.01); *A61B 5/746* (2013.01); *A63B 71/085* (2013.01); *A61B 5/02438* (2013.01); *A61B 5/038* (2013.01); *A61B 5/6817* (2013.01); *A61B 5/6819* (2013.01); *A61B 2562/0257* (2013.01); *A63B 2071/0627* (2013.01); *A63B 2220/34* (2013.01); *A63B 2220/40* (2013.01); *A63B 2220/803* (2013.01); *A63B 2220/805* (2013.01)

(58) Field of Classification Search
CPC ..... A61B 5/682; A61B 5/7282; A61B 5/0004; A61B 5/0205; A61B 5/7267; A61B 5/1121; A61B 5/746; A61B 5/7257; A63B 71/085; A63B 2220/40; A63B 2220/803; A63B 2220/805; A63B 2071/086; A63B 2071/088
See application file for complete search history.

(56) References Cited

U.S. PATENT DOCUMENTS 5,122,796 A * 6/1992 Beggs .................. G01S 7/4811
                                                                      180/169
6,522,266 B1 * 2/2003 Soehren ............... A61B 5/7264
                                                                      340/988

(Continued)

*Primary Examiner* — Christopher A Flory
*Assistant Examiner* — Vynn Huh
(74) *Attorney, Agent, or Firm* — Foley & Lardner LLP; Cliff Z. Liu

(57) ABSTRACT

Provided is a device for placement on a human subject to detect impacts on the human subject. The device includes a base member, one or more engagement sensors to detect whether the device is properly placed on the human subject, and one or more motion sensors to detect the kinematics of the human subject. The device also includes a processing unit that includes methodology to detect false positives such as chewing, dropping, and throwing.

25 Claims, 19 Drawing Sheets

(51) Int. Cl.
  *A61B 5/11*    (2006.01)
  *A63B 71/08*   (2006.01)
  *A61B 5/024*   (2006.01)
  *A61B 5/08*    (2006.01)
  *A61B 5/03*    (2006.01)
  *A63B 71/06*   (2006.01)

(56) References Cited

U.S. PATENT DOCUMENTS

| | | |
|---|---|---|
| 6,826,509 B2 | 11/2004 | Crisco et al. |
| 6,941,952 B1 | 9/2005 | Rush, III |
| 7,526,389 B2 | 4/2009 | Greenwald et al. |
| 8,548,768 B2 | 10/2013 | Greenwald et al. |
| 8,554,509 B2 | 10/2013 | Crisco et al. |
| 2005/0177929 A1* | 8/2005 | Greenwald ............ A42B 3/046 2/425 |
| 2006/0166157 A1* | 7/2006 | Rahman ............... A61B 5/4833 433/6 |
| 2009/0041313 A1* | 2/2009 | Brown .................. H04M 1/05 382/124 |
| 2010/0274100 A1* | 10/2010 | Behar ................. A61B 5/0002 600/301 |
| 2011/0179851 A1* | 7/2011 | Mack .................... A42B 3/046 73/1.79 |
| 2011/0184319 A1 | 7/2011 | Mack et al. |
| 2012/0143526 A1* | 6/2012 | Benzel .................. A42B 3/046 702/42 |
| 2012/0210498 A1* | 8/2012 | Mack .................. A42B 3/0466 2/414 |
| 2012/0220893 A1* | 8/2012 | Benzel .................. A42B 3/046 600/553 |
| 2012/0229248 A1* | 9/2012 | Parshionikar .......... G08B 21/06 340/3.1 |

* cited by examiner

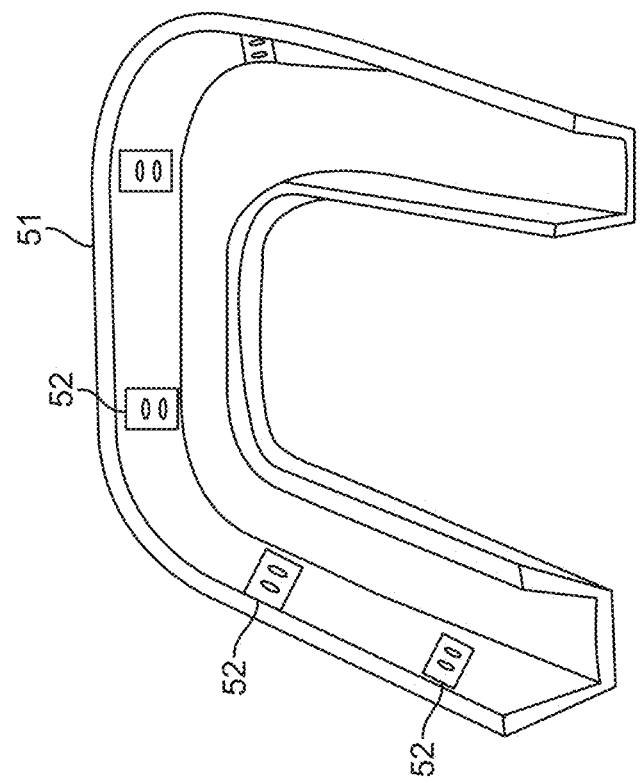
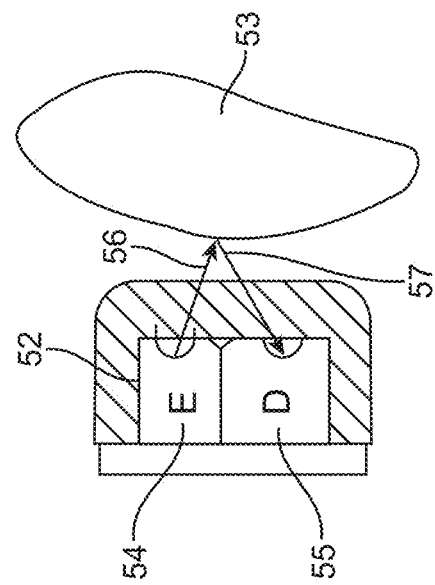
FIG. 5A
FIG. 5B

DEVICE FOR DETECTING ON-BODY IMPACTS

CROSS REFERENCE TO RELATED APPLICATION

This application claims the benefit of U.S. Provisional Application Ser. No. 61/775,411 filed on Mar. 8, 2013, the disclosure of which is incorporated herein by reference in its entirety.

This invention was made with the Government support under contract EB017611 awarded by the national Institute of Health. The Government has certain rights in the invention.

FIELD OF THE DISCLOSURE

The present disclosure, in general, relates to devices and methods for detecting collisions in sports, healthcare, and other applications. In particular, a device includes sensors and methodology for detecting on-body impacts while screening out false positive movements such as chewing, dislodging, dropping, and throwing.

BACKGROUND

The following discussion of the background of the disclosure is merely provided to aid the reader in understanding the disclosure and is not admitted to describe or constitute prior art to the present disclosure.

The Centers for Disease Control and Prevention (CDC) estimates over 300,000 sports related concussions occurring each year. In 2009, the State of Washington passed the Lystedt law, named after Zackery Lystedt who suffered a brain hemorrhage and was paralyzed after receiving two severe head blows during a junior high football game. While such catastrophic events are rare, sustaining a single concussion increases one's risk of re-injury by 2 to 6 times with associated delayed recovery of cognitive, memory, and mood symptoms. Therefore, it is important to accurately identify athletes that have been concussed to prevent re-injury. The Lystedt law, now ratified in 42 states, requires youth athletes to be removed from play whenever a head injury is suspected to have occurred. The intent of the law is on target, but unfortunately concussion is an "invisible" injury and often goes undetected. The lack of an objective injury measurement solution is further complicated by a sports culture that often promotes playing through injury.

To protect young athletes, there is a need for an objective diagnostic tool to aid parents, coaches, and clinicians to make the decision to remove injured athletes from play.

SUMMARY

Certain embodiments of the present disclosure relate to devices and methods for detecting impact in sports activities and predicting the likelihood of injury. Because athletes may engage in many different movements on sports fields, devices and methods for impact detection are desirable to have both good sensitivity and good accuracy. In some embodiments, a device for impact detection can process both placement data of the device relative to a human subject and impact data from embedded motion sensors to screen out spurious high-acceleration non-impact movements. In some embodiments, statistical pattern recognition or other machine learning methods can be employed to further improve the sensitivity and accuracy.

The present disclosure provides, in one embodiment, an oral appliance including: (1) a base member having a generally U-shaped form defining a channel to receive a row of teeth of a human subject; (2) an emitter affixed to the base member, where the emitter is operable to emit a wave signal; (3) a receiver affixed to the base member, where the receiver is positioned relative to the emitter such that the receiver is operable to detect a reflected wave signal when the base member is placed on the row of teeth; and (4) a motion sensor affixed to the base member, where the motion sensor includes at least one of an accelerometer and a gyroscope.

In some embodiments, the oral appliance further includes a light sensor affixed to the base member and operable to detect ambient light.

In some embodiments, the oral appliance further includes a processor in electronic communication with the receiver and the motion sensor, where the processor is operable to process data received from the receiver and the motion sensor using a machine learning technique to identify a head collision.

In some embodiments, the machine learning technique is a support vector machine (SVM) classifier.

Also provided, in some embodiments, is a device for motion event classification, including: (1) a base member; (2) an engagement sensor affixed to the base member, where the engagement sensor is operable to detect a placement of the base member on a human subject; (3) a motion sensor affixed to the base member; and (4) a processor in electronic communication with the engagement sensor and the motion sensor, where the processor is operable to classify an event based on data received from the engagement sensor and the motion sensor during the event.

In some embodiments, the base member of the device includes one of a mouthguard, a tooth patch, an ear plug, a body patch, and a nose patch.

In some embodiments, the engagement sensor of the device includes at least one of a proximity sensor, an interruption sensor, a pressure sensor, a strain sensor, a pulse oximeter, and a multi-directional sensor.

In some embodiments, the motion sensor of the device includes at least one of a linear acceleration sensor and a rotational velocity sensor.

In some embodiments of the device, the motion sensor includes at least one of a multi-axial accelerometer and a multi-axial gyroscope.

In some embodiments, the device further includes a light sensor affixed to the base member and operable to detect ambient light.

In some embodiments, the device further includes an alert generator for indicating the event.

In some embodiments, the device further includes a memory in electronic communication with the processor. The memory stores program code which, when executed by the processor, is operable to process the data received from the engagement sensor and the motion sensor during an event to classify the event.

In some embodiments, the program code in the memory is operable to classify an event as an on-body event based on detection of the placement of the base member on the human subject during the event.

In some embodiments, the program code is configured to execute a machine learning technique to classify the event.

In some embodiments, the machine learning technique is a SVM classifier.

In some embodiments, the SVM classifier is operable to classify the event based on frequency domain features of the data received from the motion sensor.

Some embodiments of the disclosure relate to a method of detecting an impact on a human subject. The method includes: (1) measuring placement data of an impact detection device relative to a human body during an event; (2) measuring motion data of the impact detection device during the event; and (3) classifying the event as an on-body, impact event based on a combination of the placement data and the motion data.

In some embodiments of the impact detection method, the event is classified as an on-body, impact event based on the placement data indicating that the impact detection device is engaged on the human body.

In some embodiments of the impact detection method, the event is classified as an on-body, impact event based on a machine learning technique.

In some embodiments of the impact detection method, the event is classified as an on-body, impact event based on frequency domain features of the motion data.

Other aspects and embodiments of the disclosure are also contemplated. The foregoing summary and the following detailed description are not meant to restrict the disclosure to any particular embodiment but are merely meant to describe some embodiments of the disclosure.

BRIEF DESCRIPTION OF THE DRAWINGS

Provided as embodiments of this disclosure are drawings which illustrate certain aspects by example, and not limitation. For a better understanding of the nature and objects of some embodiments of the disclosure, reference should be made to the following detailed description taken in conjunction with the accompanying drawings, wherein:

FIG. 5A, FIG. 5B, and FIG. 5C illustrate a device with one or more reflective engagement sensors;

Some or all of the figures are schematic representations by way of example; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Certain embodiments of the present disclosure relate to devices that detect head collision with low false positive rates. Instrumented mouthguards are well-suited for head impact detection because they can be custom made to fit the upper or lower jaw and directly measure skull kinematics. However, an impact detection method according to a fixed threshold may falsely detect many spurious high-acceleration non-impact events as on-body impacts. Some of these non-impact events may be generated by manual manipulation of the device, and some could come from device insertion or removal. A higher threshold could help to improve accuracy but will sacrifice sensitivity. These misclassified events will skew conclusion and raise false positives when screening for head trauma.

Figure 1A:
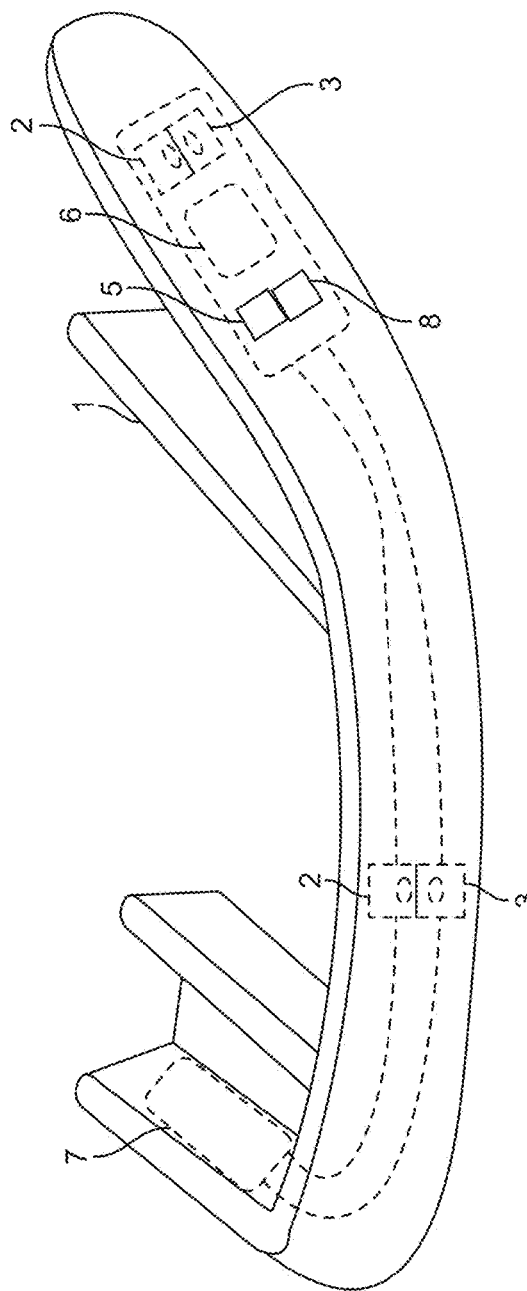
FIG. 1A and FIG. 1B illustrate an oral appliance with one or more emitter and receiver pairs.
Figure 1B:
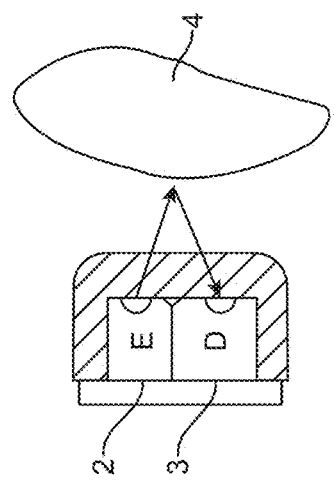

In some embodiments of the present disclosure as depicted in FIG. 1, a device is an oral appliance, which includes: (a) a base member 1 having a generally U-shaped form defining a channel to receive a row of teeth 4 of a human subject; (b) an emitter 2 affixed to the base member 1, where the emitter 2 is operable to emit a wave signal, such as one or more of an electromagnetic wave, an acoustic wave, an optical wave, and a pulse wave; (c) a receiver 3 affixed to the base member 1, where the receiver 3 is positioned relative to the emitter 2 such that the receiver 3 is operable to detect a reflected wave signal when the base member 1 is placed on the row of teeth 4, while no wave signal or a weak signal is reflected to the receiver 3 when the base member 1 is not properly engaged on the row of teeth 4; and (d) a motion sensor 5 affixed to the base member 1, where the motion sensor 5 includes at least one of an accelerometer and a gyroscope.

According to some embodiments, the device may also include a plurality of emitters 2 and receivers 3. As depicted in FIG. 1, the device also includes a processor 6 and a rechargeable battery 7. Data from the motion sensor 5 and receiver 3 can be analyzed by the processor 6. The device further includes a light sensor 8 as illustrated in FIG. 1. The light sensor 8, such as an ambient light sensor, can be placed and used to detect light such that, when the device falls out of the mouth or is otherwise exposed to environmental light, the sensor 8 determines that any detection of potential head collision is likely a false positive.

In some embodiments, the device is designed to minimize the motion and displacement between the base member and the human subject. However, even with relative motion and displacement between the device and the human subject minimized, there are still some non-impact events, such as insertion, removal, chewing, clenching, drinking, and spitting, that could trigger false positive detection. In some embodiments of the present disclosure, the impact detection device distinguishes on-body impacts from non-impact and off-body events by training and optimizing two classification subsystems. First, an engagement sensor determines if the device is worn properly on the body of a human subject. All events in which improper engagement is detected are filtered out. Second, on-body, non-impact events are rejected using a machine learning technique, where the device is trained on features in data measured by a motion sensor.

Also provided, in some embodiments, are devices to be applied on other body parts of a human subject for the detection of motion impacts. Like the oral devices, these devices can include a base member for affixing the devices to a body part, a sensor to detect whether the devices are fully engaged on the body parts, and an accelerometer or a gyroscope for detecting motions. Processing units and computer software can also be embedded in these devices.

1. Base Member

In some embodiments, a base member can be a mouthguard that is used by athletes. The base member, in some embodiments, has a generally U-shaped form defining a channel to receive an upper or lower row of teeth of a human subject as illustrated in FIG. 1.

A base member can be custom made to fit a human subject's dental stone. For example, pictures of the teeth can be taken from multiple measured angles using a camera or a smart phone and sent to a manufacturer, who will then reconstruct a three dimensional (3-D) model of the subject's teeth. Subsequently, a dental stone may be fabricated via a method such as 3-D printing, and be used to vacuum form the base member.

Another method to make the base member is to provide the customer with a dental impression kit with tools and instructions for taking a dental imprint, which will be mailed back to the manufacturer for the fabrication of a dental stone.

In some embodiments, the base member is made of a biocompatible material. In some embodiments, the base member is long enough to cover at least 6 teeth, 8 teeth, 10 teeth, or 12 teeth of a human youth. In some embodiments, the base member is at least about 4 centimeter (cm) long or alternatively at least about 6 or 8 cm long. In some embodiments, the base member includes a channel to receive the teeth, and the channel is at least about 0.4, 0.5, 0.6, 0.7, or 0.8 cm deep.

Figure 2:
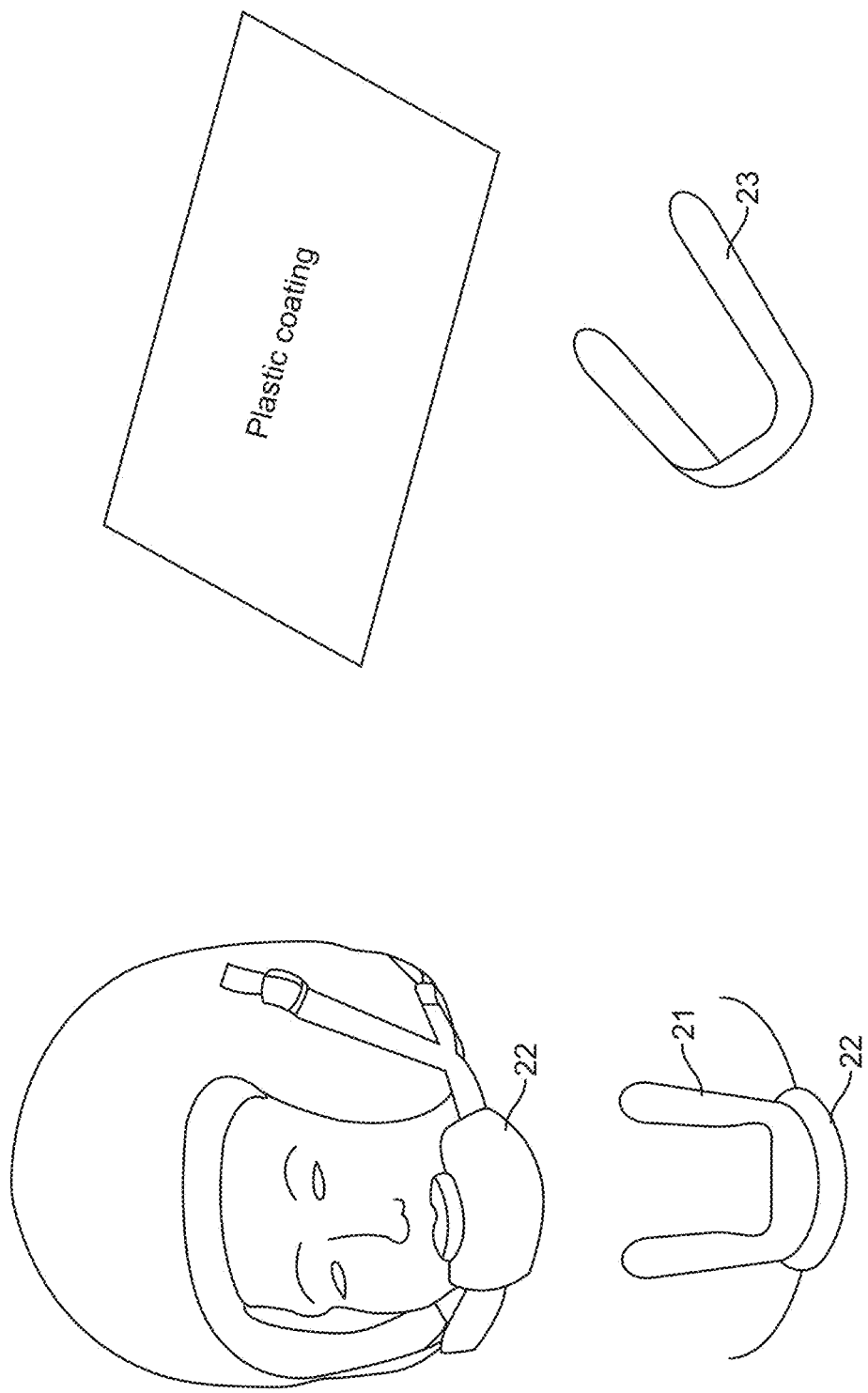
FIG. 2 illustrates a base member with a metal frame or being attached to a chinstrap.

One way of minimizing relative motion and displacement between the device and the center of mass of a human head is to increase the effective mass of the base member such that it does not move as easily as light-weight mouthguards. Ways to achieve this include attaching a base member 21 to a chinstrap 22, or using a heavier filling, such as a metal frame 23, in the base member 21 as depicted in FIG. 2.

Figure 3:
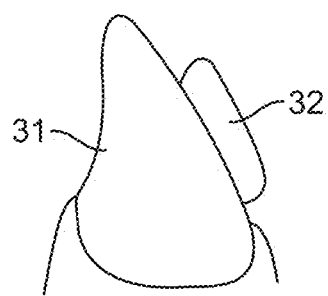
FIG. 3 illustrates a base member in the form of a tooth patch.

In some embodiments, as depicted in FIG. 3, the base member is a tooth patch 32 that is securely attached to one or more of a human subject's teeth 31. The tooth patch 32 may contain an accelerometer or other sensors for data collection.

Figure 4:
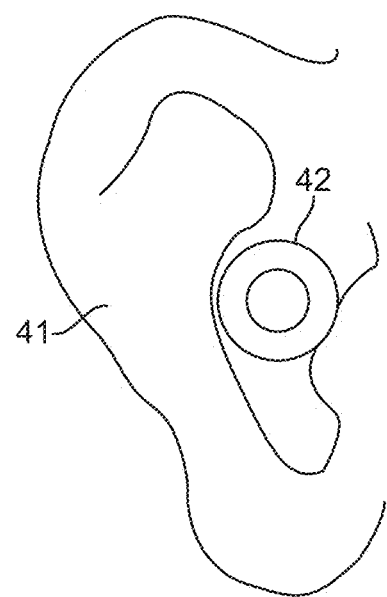
FIG. 4 illustrates a base member in the form of an earplug.

In some embodiments, the base member takes the form of an earplug 42 such that it can be placed in a human subject's ear 41 as shown in FIG. 4. In such embodiments, the base member has an outer contour that complements the inner channel of an outer section, and optionally a middle section, of the ear 41. To avoid interfering with the human subject's hearing abilities, the base member can be made hollow or have a microphone and speaker pair to aid in hearing.

In some embodiments, the base member is a patch for affixing to a human subject's skin. The patch can be attached directly to the human subject's head, ear studs, nose studs, or any form of implants on the head with minimal relative motion between the implants and the center of mass of the head.

2. Engagement Sensing

Certain aspects of the present disclosure relate to optimized engagement sensing for detecting a dislocation of an impact detection device from a human subject. In some embodiments, the device includes one or more sensors to determine whether the device is properly engaged on teeth or other body parts of a human subject.

a. Proximity Sensing

Figure 5C:
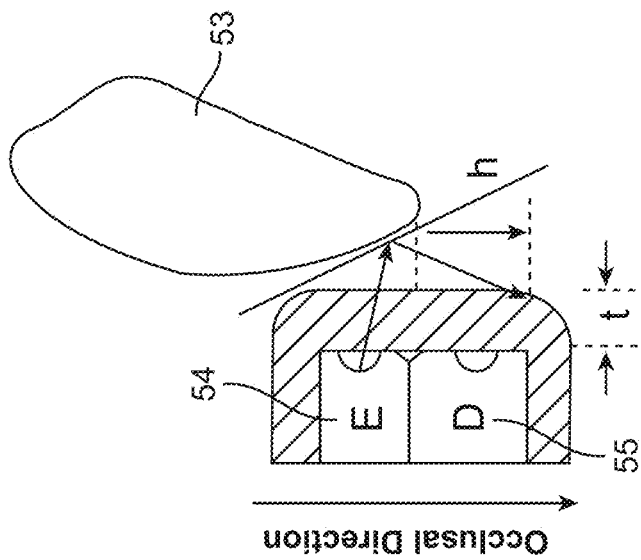
Figure 5C:
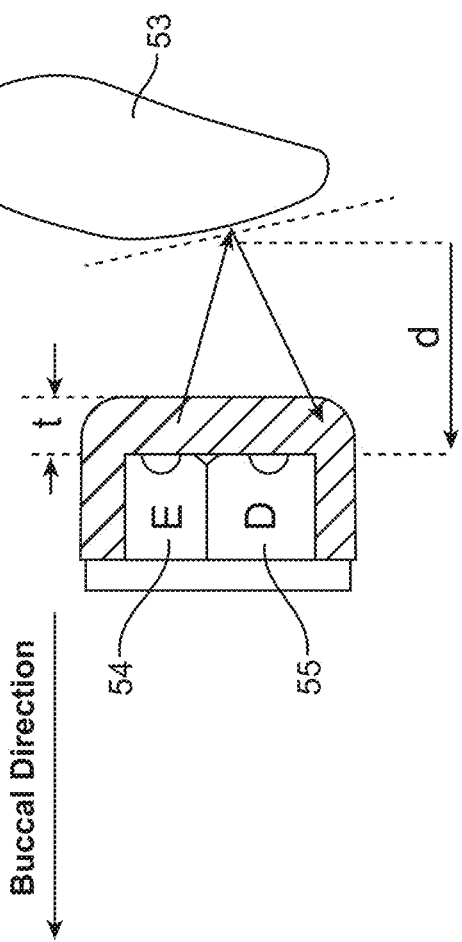

In one embodiment as depicted in FIG. 5A and FIG. 5B, the device includes one or more emitter and receiver pairs 52, where an emitter 54 transmits a wave signal 56, which can be detected by a receiver 55 when properly reflected. The emitter and receiver pair 52 is placed on a base member 51 such that when the base member 51 is fully engaged on a row of teeth 53, one or more of the teeth reflect the wave signal 56 such that a reflected signal 57 reaches the receiver 55 for detection. For instance, as illustrated in FIG. 5B, the emitter and receiver pair 52 is placed close to a surface of the base member 51 facing the teeth 53, in close proximity. When not fully engaged, the wave signal does not reflect properly to the receiver 55 and thus the receiver 55 cannot detect the signal or can detect a reduced portion of the signal, as depicted in FIG. 5C. In some embodiments, the device includes two or more such emitter and receiver pairs 52 to further improve the detection accuracy.

Since the base member 51 can move in a direction perpendicular or parallel to a tooth surface, the engagement sensor can be positioned and trained based on outputs measured when the base member 51 is moved away from the tooth surface (buccal) and towards the bite plane (occlusal) as illustrated in FIG. 5C. In addition, a thickness t of the base member material can be determined for optimum engagement sensing.

The wave signal 56 transmitted from the emitter 54, in some embodiments, is an infrared signal. Other types of signals can also be used, such as capacitive, inductive, radio frequency, electromagnetic field distortion, radar, sonar, ultrasonic, impedance, and conductivity signals.

In some embodiments, the emitter and receiver pair for the engagement sensing does not have to be powered continuously. Pulsing the emitter and the receiver can reduce the power consumption of the device. A sensor with lower power consumption, such as one based on pure conductance, can be used to determine whether the device is in-mouth before the emitter and the receiver are activated. Further, pulsing the emitter at a prescribed frequency will allow the filtering of extraneous noise signals which may be received at other frequencies.

b. Pressure Sensing

Figure 6:
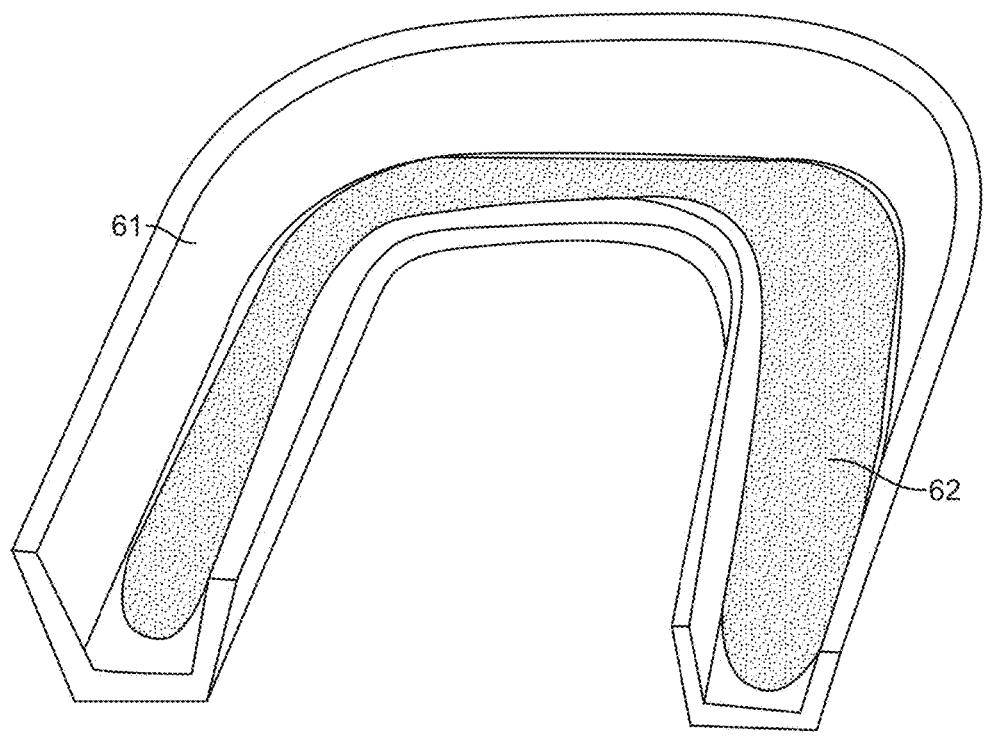
FIG. 6 illustrates a device with a pressure sensor.

In some embodiments as depicted in FIG. 6, the device includes one or more pressure sensors 62 on a base member 61 to measure pressures applied on the base member 61 when the device is placed on a row of teeth. In some embodiments, the pressure sensor 62 is placed on a surface of the base member 61 facing the teeth. In some embodiments, the pressure sensor 62 and the base member 61 are configured, for example, to have a channel that is slightly smaller than the size of the teeth, such that when they are in contact with the teeth, a pressure is generated from such contact.

c. Interruption Sensing

Figure 7B:
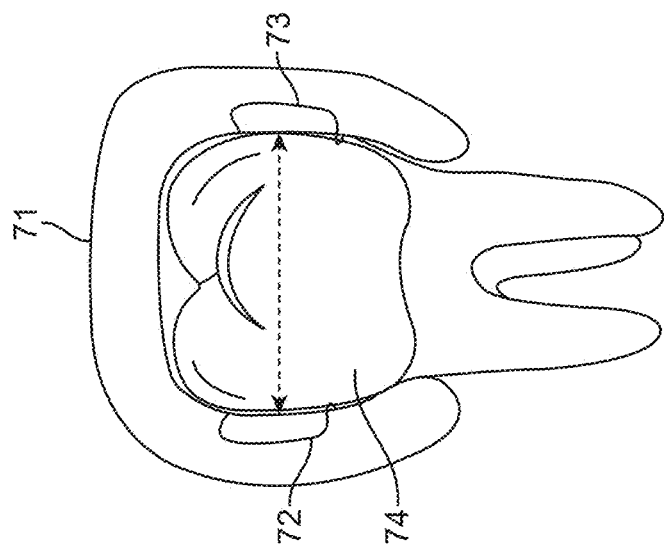
FIG. 7A and FIG. 7B illustrate a device with a pair of interruption sensors.
Figure 7A:
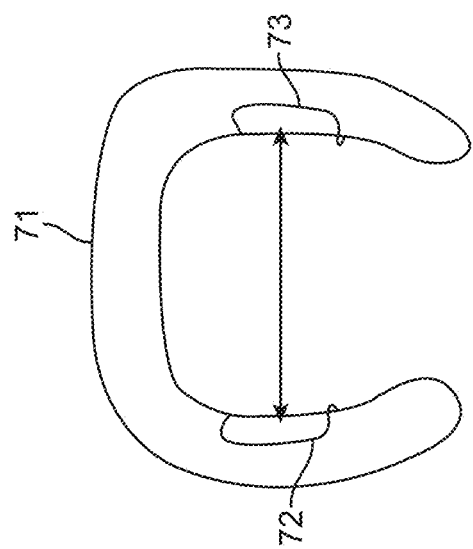

In some embodiments, the device includes an interruption sensor which includes an emitter and a receiver for transmitting and detecting a wave signal. The emitter and the receiver are placed on the base member such that when the device is fully engaged on one or more teeth 74, the wave signal from the emitter is blocked by the teeth 74, and little or no signal is detected by the receiver; when the device is not engaged on the teeth 74, the signal from the emitter can be detected by the receiver. For instance, an emitter 72 and a receiver 73 can be installed on opposite sides of the channel of a base member 71 as depicted in FIG. 7.

d. Strain Sensing in a Pre-Stressed Base Member

Figure 8C:
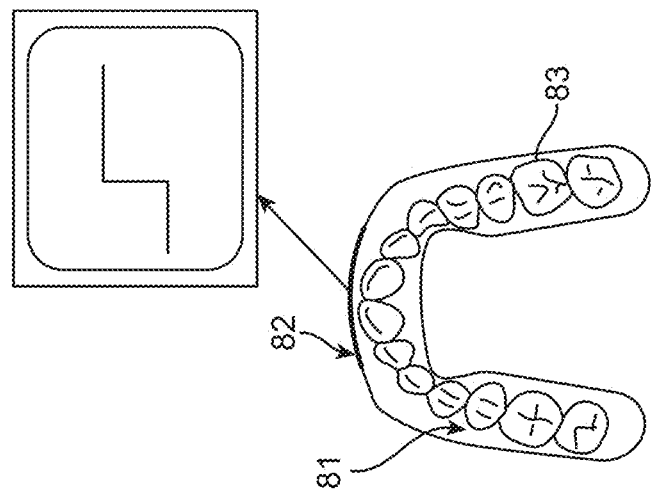
FIG. 8A, FIG. 8B, and FIG. 8C illustrate the use of a strain sensor with a pre-stressed base member.
Figure 8B:
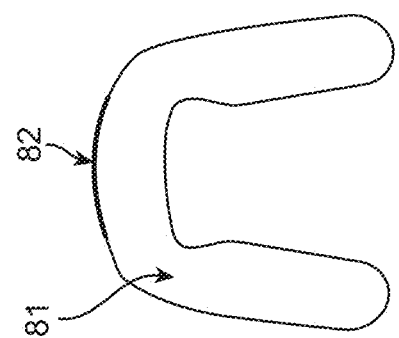
Figure 8A:
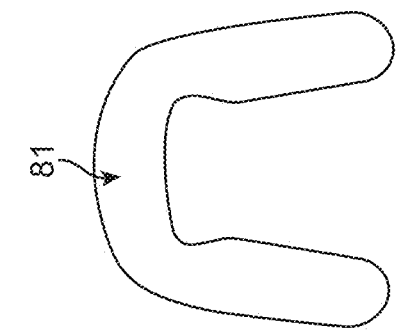

As illustrated in FIG. 8, in some embodiments, a base member 81 is pre-stressed such that it will not be a perfect fit for a human subject's teeth 83. As a result, when the base member 81 is placed on the teeth 83, there will be a strain within the base member 81, which could be sensed by a sensor such as a strain gauge 82 to indicate whether the base member 81 is engaged on the teeth 83.

e. Pulse Oximeter

Figure 9:
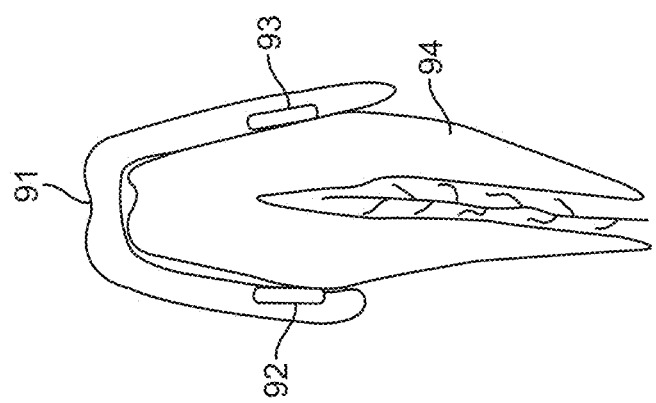
FIG. 9 illustrates a device with a pulse oximeter for detecting pulses in a tooth.

In some embodiments, the device includes an oximeter emitter-receiver pair 92 and 93 on a base member 91 as depicted in FIG. 9. Teeth 94 contain blood vessels, which generate pulses. The oximeter emitter-receiver pair 92 and 93, therefore, is able to determine whether the base member 91 is placed on the teeth 94 by detecting the pulses from the blood vessels.

f. Multi-Directional Signal Emitter and Receiver

Figure 10:
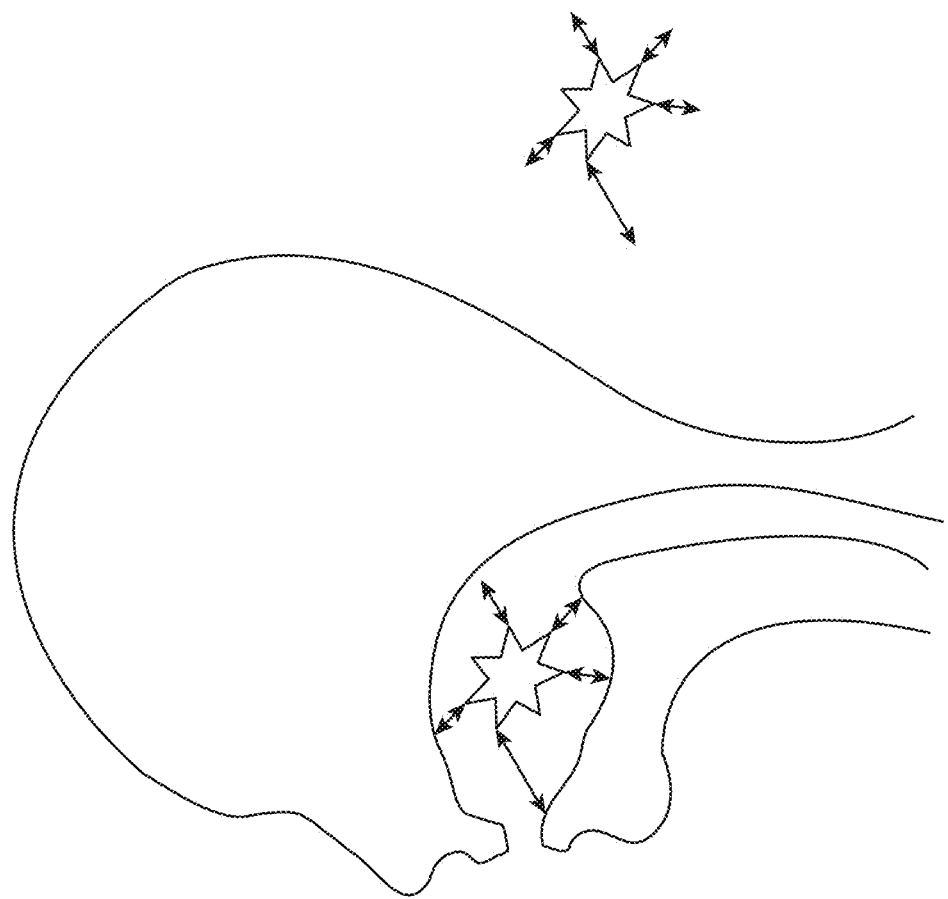
FIG. 10 illustrates the rationale of using a multi-directional or omni-directional sensor.

A mouth represents a confined space. Therefore, a multi-directional or omni-directional sensor can be installed at an appropriate location on a base member to sense the confinement of the device within the mouth. FIG. 10 illustrates the rationale of this sensor. By detecting the reflected signals from the interior of the mouth, data generated from the multi-directional sensor can be used to calculate the location of the device within the mouth, from which whether the device is fully engaged on teeth can be derived.

3. Motion Sensing

In some embodiments, the device includes either, or both, a linear acceleration sensor, such as an accelerometer, and a rotational velocity sensor, such as a gyroscope, which detects motion of the device on a human subject. In some embodiments, the accelerometer is a multi-axial accelerometer, such as a tri-axial accelerometer or a dual-axial accelerometer. In some embodiments, the rotational velocity sensor is a multi-axial gyroscope, such as a dual-axial gyroscope or a tri-axial gyroscope. In some embodiments, other combinations of one or more single-axial and multi-axial accelerometers and gyroscopes can be used to measure magnitudes and directions of motion.

In some embodiments, an accelerometer measures a proper acceleration associated with the phenomenon of weight experienced by any test mass at rest in the frame of reference of the accelerometer device. Single-axial and multi-axial accelerometers can be used to detect the magnitude and direction of the proper acceleration (or g-force), as a vector quantity, and can be used to sense orientation, coordinate acceleration, vibration, shock, and falling in a resistive medium.

In some embodiments, a gyroscope is a device for measuring or maintaining orientation based on the principle of angular momentum. Mechanically in some embodiments, a gyroscope is a spinning wheel or disk whose axle is free to assume any orientation. Although this orientation does not remain fixed, it changes in response to an external torque less and in a different direction than it would without a large angular momentum associated with the disk's high rate of spin and moment of inertia. Gyroscopes can take on many forms based on different operating principles, such as micro-electro-mechanical-system (MEMS) gyroscopes, solid-state ring lasers, fiber optic gyroscopes, and quantum gyroscopes.

4. Signal Processing and Impact Detection

Figure 11:
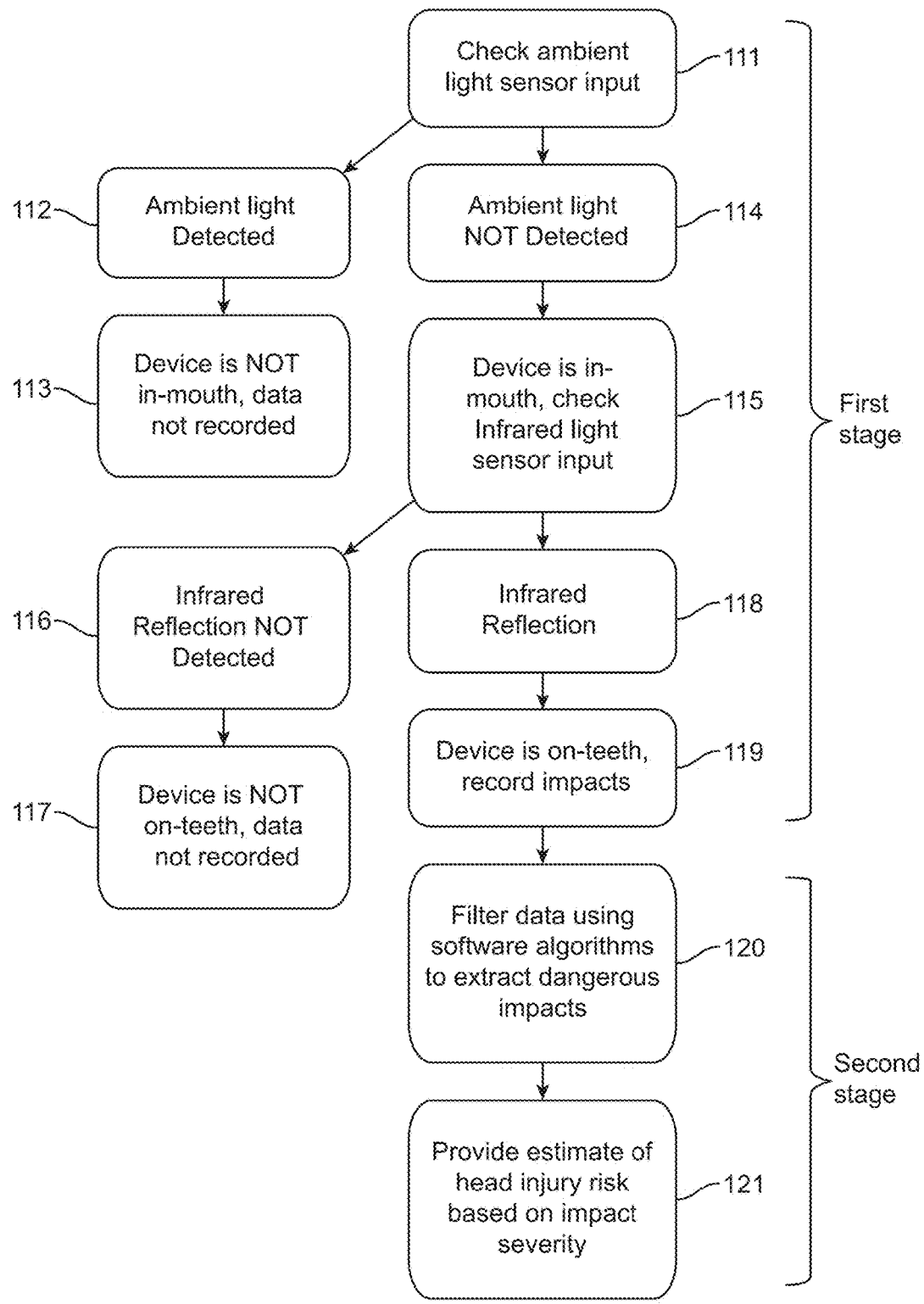
FIG. 11 illustrates a data processing methodology.

In some embodiments, the device further includes a memory and a processor for receiving and processing data collected from sensors to detect on-body impacts. The memory can be any non-transitory computer-readable storage medium storing program code for implementing software methodologies described in the present disclosure. In some embodiments, the impact detection is accomplished in two stages. One such data processing methodology for the impact detection is illustrated in FIG. 11 and described below.

a. Off-Body Event Classifier

According to some embodiments, in a first stage (blocks 111-119), an ambient light sensor and an engagement sensor, such as an infrared proximity sensor, a pressure sensor, an interruption sensor, a strain sensor, and other suitable sensors described in the present disclosure, detect whether the device is fully engaged on body parts like teeth. Unambiguous false positives, occurring when the device is out of the mouth or otherwise not in use, could be rejected by the ambient light sensor (blocks 111-113).

When a device is in-mouth but is not fully engaged on the teeth, motions of a human subject's head would not be reliably measured by the device. Events triggered by these motions when the device is not fully engaged on the teeth can be rejected by an engagement sensor on the device (blocks 115-117). In some embodiments, the engagement sensor can include an emitter paired with a receiver. When the device is fully engaged on the teeth, the signal transmitted from the emitter reflects off the teeth and back to the receiver. When the device is moved away from the full engagement position, no signal or a weak signal is reflected to the receiver. Therefore, events during which the device is not fully engaged on teeth can be rejected as non-impact events based on the strength of the received signal at the receiver (blocks 115-117).

b. On-Body Impact Event Classifier

In a second stage (blocks 120-121), software methodologies filter out false alarm events which occur when the device is properly engaged on a human subject. Data from motion sensors can be classified as true or false on-body impacts using various signal processing techniques. Waveform features, such as pulse width, relative spectral power, quality factor, and pulse height, can be used to further aid in the classification.

In some embodiments, kinematic thresholds, such as a peak linear acceleration, can be used to filter out noise events. A low pass filter can be pre-applied to motion signals associated with an event, and a filtered threshold can then be used to classify the event. Measurements of events where the peak linear acceleration is below the threshold are assumed to be noise.

In some embodiments, the signal processing techniques include statistical pattern recognition methods and other machine learning techniques, such as a SVM classifier. In one embodiment, power spectral density of motion sensor data associated with an event is used as a feature vector from which the event is classified as either an on-body impact or a non-impact event. The SVM classifier can be trained using labeled impact data and labeled false alarm data recorded from real events. The classification methodology can provide confidence measures for each classification as well.

In some embodiments, a dynamic model of a human head and neck system can be used to classify events. For example, a natural frequency of a simple spring-mass model for simulating impact and non-impact events is proportional to $\sqrt{k/m}$, where k is the stiffness, and m is the mass of the system. During non-impact events, the device is mainly moving on its own and interacting with stiff objects such as helmets and ground. During on-body impacts, however, the device is tightly coupled to a helmeted head mounted on a flexible neck. With much higher masses of colliding objects and lower stiffness of the flexible neck, the on-body impacts have lower natural frequencies than non-impact events. Given dynamic parameters for a system, kinematic waveforms measured by motion sensors can be fitted to the impulse response of the system. The quality of the fit can be used as a criterion for classification.

Statistical methods, such as naive Bayes and logistic regression methods, can also be applied to data measured by the sensors during an event to classify the event.

c. Helmet Microphone

Figure 12:
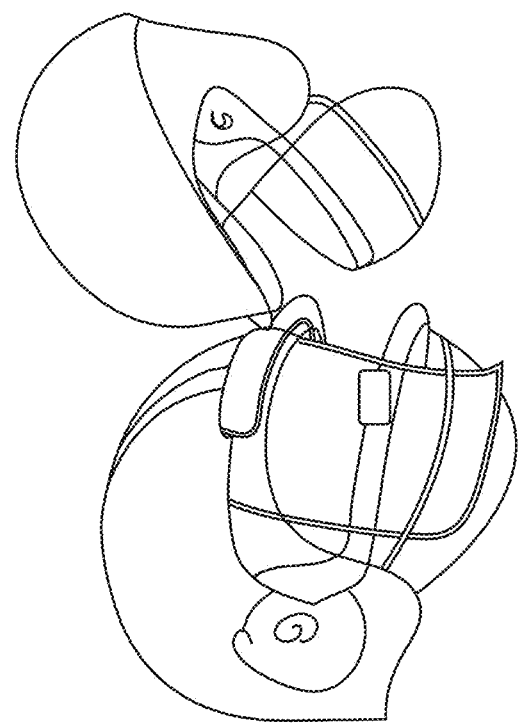
FIG. 12 illustrates the addition of a microphone for aiding event classification.
Figure 12:
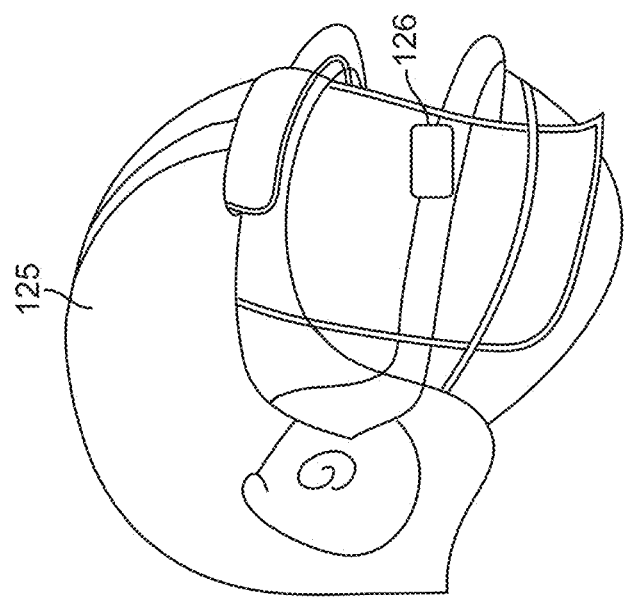

In some embodiments, as illustrated in FIG. 12, a microphone 126 can be installed on a helmet 125 of a human subject to record sound signals. The recorded signals can include sounds coming from head impacts, speaking, and other sounds on sports fields. By applying suitable classification methods, such signals can aid in determining whether a hit recorded by sensors worn by a user is a true head impact or arises from other noise sources.

EXAMPLES

The present disclosure will be understood more readily by referring to the following examples, which are provided by way of illustration and are not intended to be limiting.

Example 1

An oral appliance for impact detection, as illustrated in FIG. 1, is instrumented with an emitter and receiver pair for measuring reflected wave signal from teeth of a human subject, a tri-axial accelerometer for measuring linear accelerations, and a tri-axial gyroscope for measuring angular velocities. The impact detection is accomplished in two stages summarized in FIG. 11.

The instrumented oral appliance is compared with a reference device with an embedded accelerometer. To filter out false positives, this reference device utilizes signal processing methods as well as a pair of metal leads. These leads short out in the presence of a saliva or moist tissue contact, but do not specifically detect fixation on teeth as the disclosed device does.

Seven typical false positive events summarized in Table 1 are recreated in a laboratory setting to test both devices' abilities to reject false positives. Specificity, which corresponds to the percentage of correctly identified false positives in this comparison, is measured on both devices, and the results are summarized in Table 1. The device of the present disclosure is able to achieve a specificity of 100% or close to 100% for all but one type of false positive events. The reference device has a much lower specificity for most types of false positive events.

TABLE 1

Comparison of Head Collision Detection Specificity between a Device of the Present Disclosure and a Reference Device

| False alarm action | Reference Device | Present Device |
|---|---|---|
| bites on mouthguard while it is in-mouth but not folly engaged on teeth | 67% | 100% |

TABLE 1-continued

Comparison of Head Collision Detection Specificity between a Device of the Present Disclosure and a Reference Device

| False alarm action | Reference Device | Present Device |
|---|---|---|
| bites on mouthguard while it is fully engaged on teeth | 77% | 70% |
| pulls fully engaged mouthguard out of mouth | 68% | 100% |
| chews on mouthguard | 68% | 100% |
| throws mouthguard and catches it | 30% | 100% |
| drops mouthguard on grass | 26% | 100% |
| puts mouthguard on helmet and drops helmet on grass | 48% | 100% |
| Total | 55% | 96% |

Example 2

In this example, a complete motion event classification device is designed and evaluated.

1. Device Design

Figure 13A:
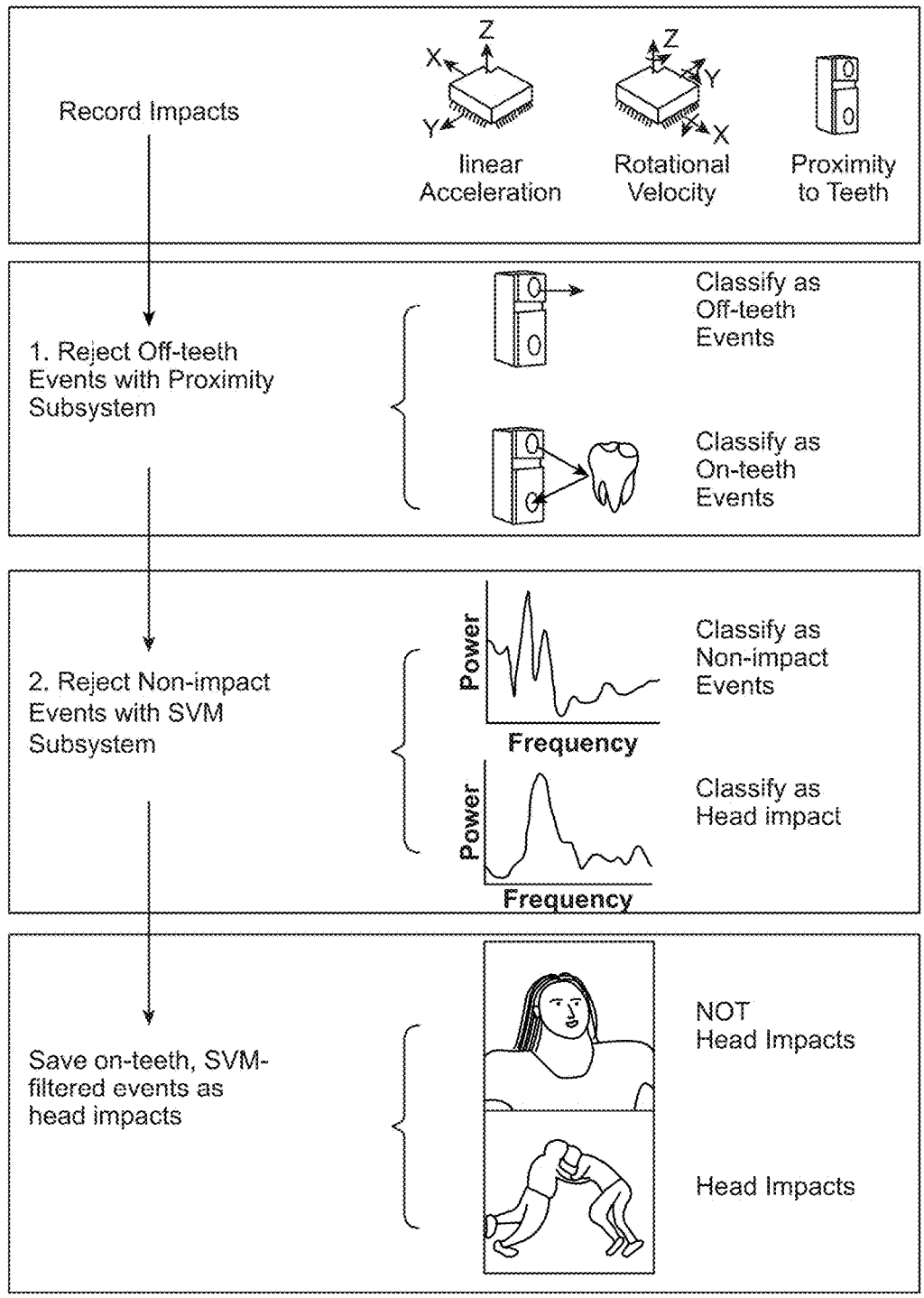
FIG. 13A and FIG. 13B illustrate a prototype of a motion event classifier.
Figure 13B:
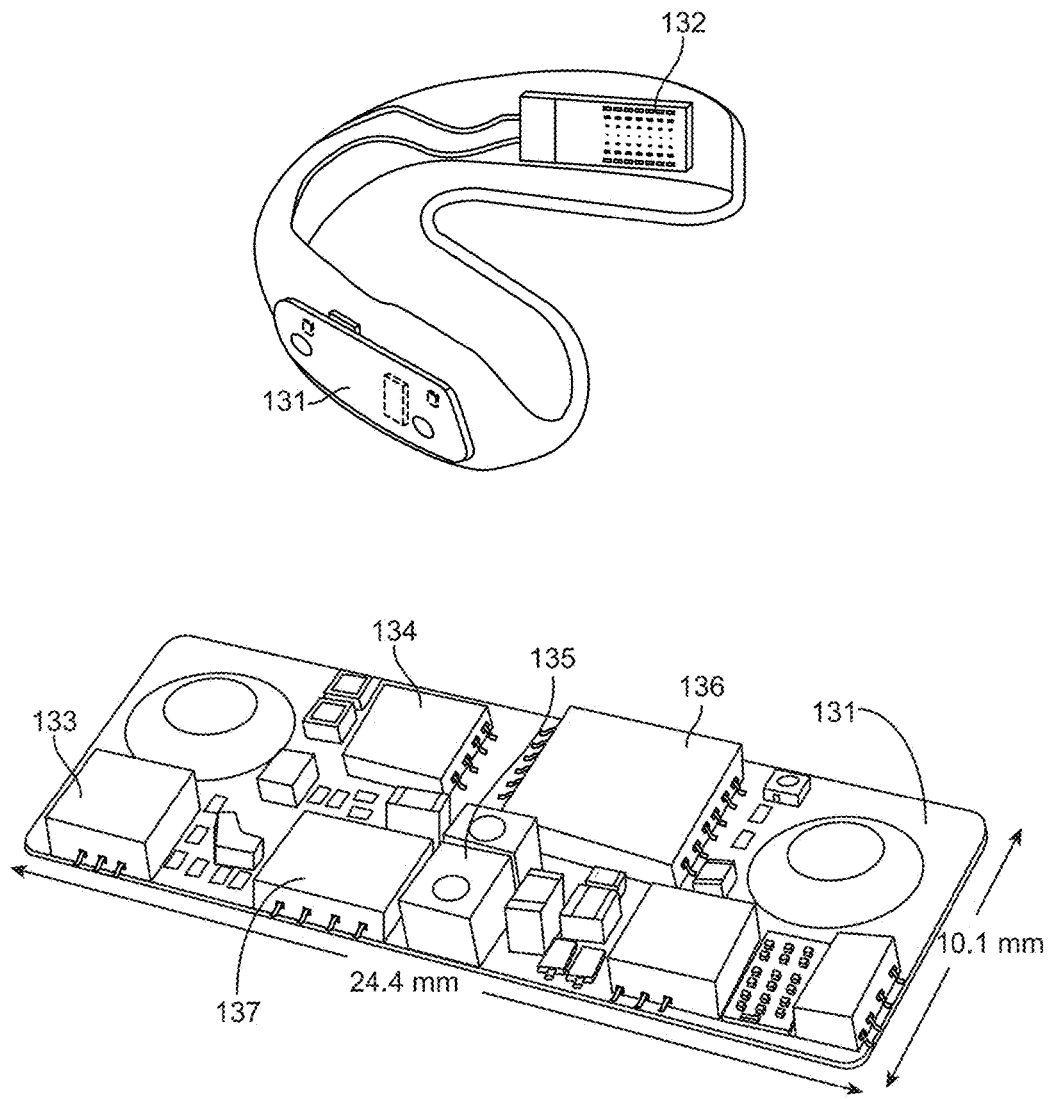

In a classification device illustrated in FIG. 13A, data are collected using an instrumented mouthguard as depicted in FIG. 13B. A tight fit of the mouthguard to a human subject's teeth is achieved by forming an ethylene vinyl acetate (EVA) material around a dental mold with a mouthguard pressure former (Great Lakes Orthodontics, Tonawanda, N.Y.). The mouthguard contains a sensor board 131 and a battery 132 sealed between two layers of EVA material. For motion and engagement sensing, the sensor board 131 is equipped with a tri-axial high range accelerometer 133 (ST H3LIS331), a tri-axial high range gyroscope 134 (Invensense ITG-3500A), and a digital proximity sensing module 135 packaged with an infrared emitter and receiver pair for near-field proximity sensing (AMS TMD2771). In addition, a microcontroller 136 (ST STM32L151) and a flash memory chip 137 (ST M25P16) allow wireless data recording and processing. Kinematic accuracy of this instrumented mouthguard is validated in a laboratory using an anthropomorphic test device.

To screen for potential head impacts, the mouthguard records all events with linear acceleration exceeding 7 g. This triggering acceleration threshold is tuned to be more sensitive than other systems with thresholds of 10 to 15 g to decrease the likelihood of missing events of interest. Linear acceleration and rotational velocity samples are collected for 10 millisecond (ms) pre-trigger and 90 ms post-trigger, with an accelerometer sampling rate of 900 to 1000 Hertz (Hz) and a gyroscope sampling rate of 800 to 900 Hz. A proximity sensor reading in 10-bit resolution is obtained at the end of the 100 ms kinematic recording period for each triggered event.

Signals collected by the engagement sensor and the motion sensor are used as inputs to two classification subsystems illustrated in FIG. 13A. To optimize the event classification device, each subsystem is designed and trained in a controlled laboratory setting.

2. Engagement Sensing Optimized to Detect Mouthguard Dislocation

Figure 14A:
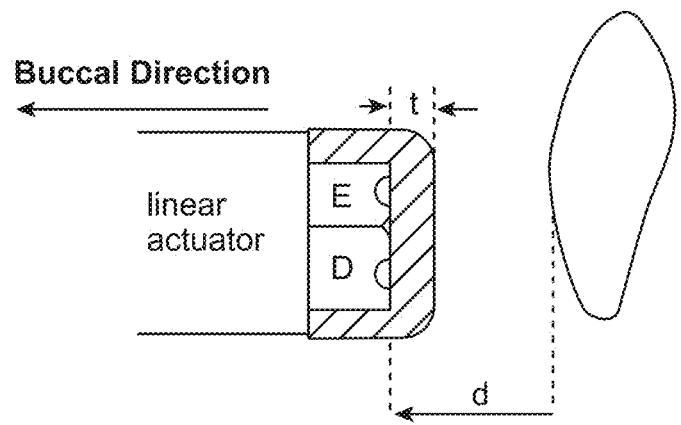
FIG. 14A and FIG. 14B illustrate a setup for characterizing an infrared proximity sensor.
Figure 14B:
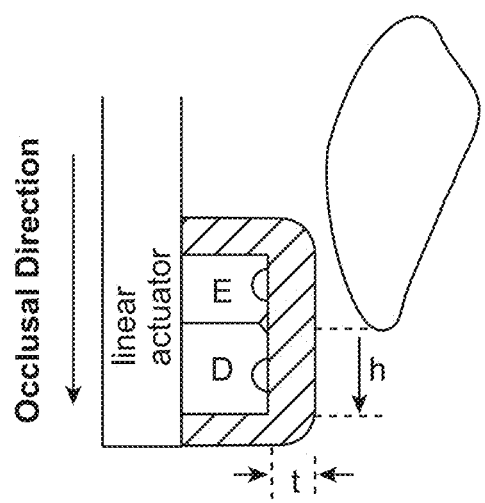

An engagement sensor, such as a proximity sensor configured for near-field detection, is used to help to reject off-teeth, non-impact events in this example. In vitro sensing behavior of an infrared proximity sensor is characterized by unit-testing sensor components. A synthetic-resin composite tooth model (Puche Dental Lab, Torrance, Calif.) that has matching optical properties as human teeth is used. Since a mouthguard can move in directions perpendicular and parallel to the tooth surface, proximity sensor outputs are measured while the mouthguard moves away from the tooth surface (buccal) and towards the bite plane (occlusal). To simulate one dimensional motion of the sensor in each direction, the sensor is attached to a linear actuator (Firgelli Technologies L12-50-100-12-P) to move away from a stationary tooth in a step of 0.5 mm as illustrated in FIG. 14A and FIG. 14B. Movement in the buccal direction d is measured from the surface of the tooth to the surface of the sensor, and movement in the occlusal direction h is measured from the bottom of the tooth to the bottom of the sensor package. To investigate effects of the EVA material, material thickness t between the sensor and the surface of the mouthguard is varied from 0 to 3 mm. Based on sensor response characteristics, sensor position and material thickness are chosen to allow the embedded proximity sensor to detect mouthguard dislocation with optimum sensitivity and accuracy.

Figure 15A:
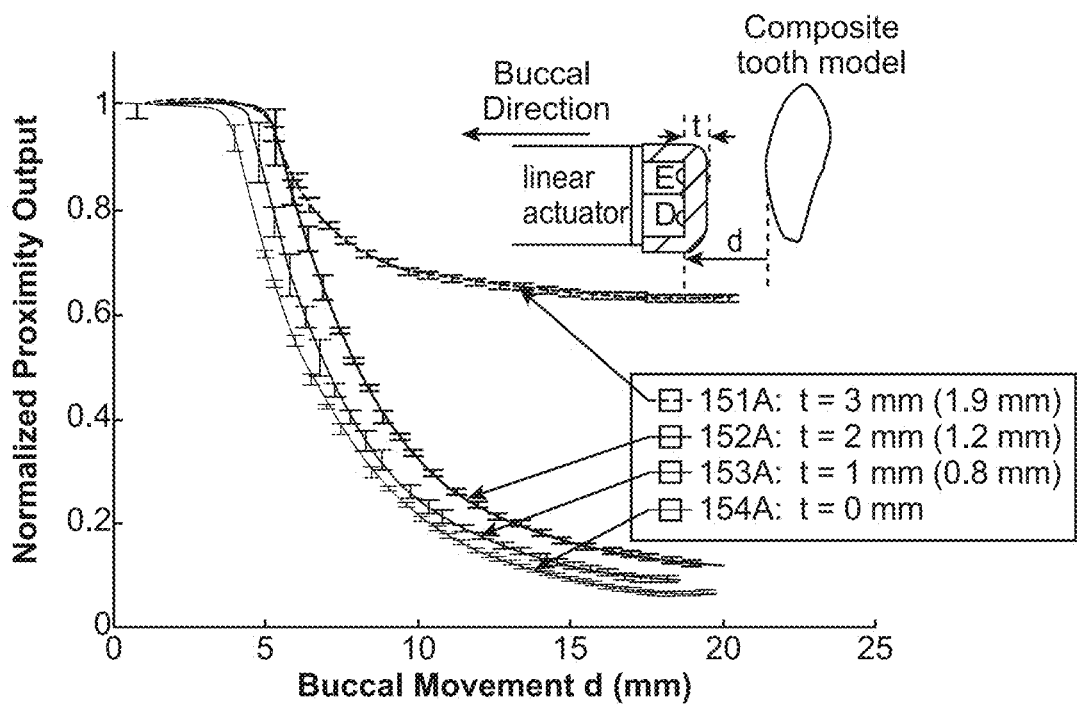
FIG. 15A and FIG. 15B illustrate the characterization results of an infrared proximity sensor.
Figure 15B:
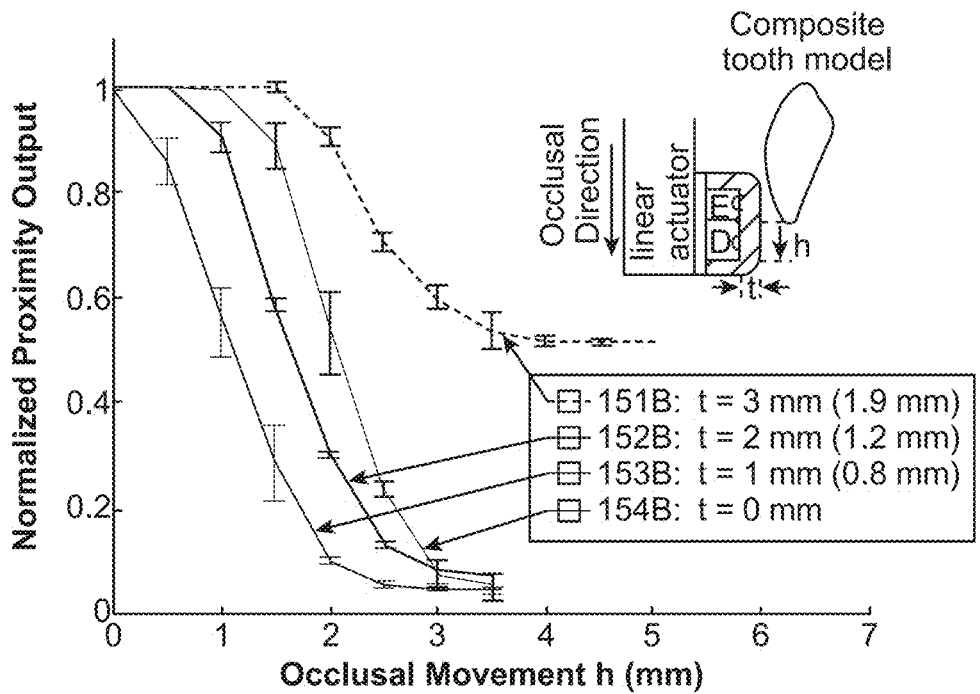

As illustrated in FIG. 15A and FIG. 15B, in vitro infrared proximity sensor output decreases monotonically with increasing buccal or occlusal displacement from a tooth. Thus, by embedding a sensor in the mouthguard to face the tooth, a device can use the infrared signal drop to detect mouthguard dislocation. The thickness of the transparent mouthguard material between the sensor and the tooth is chosen to be 2 mm because a thicker material leads to an increased signal backscattering and much higher output at larger displacements as shown by line 151A in FIG. 15A and line 151B in FIG. 15B. For teeth protection, EVA material thinner than 2 mm is not chosen in order to maintain sufficient overall mouthguard thickness with two layers of material.

Even when configured with the lowest available emitter signal strength for near-field sensing, the sensor saturates at close proximity to a tooth in both the occlusal and the buccal directions as shown by lines 151A-154A in FIG. 15A and lines 151B-154B in FIG. 15B. In these saturation regions, changes in displacement cannot be readily detected by the sensor. With the chosen material thickness of 2 mm, the 6 mm saturation region in the buccal direction shown in FIG. 15A cannot be fully avoided. However, the 1 mm occlusal saturation region shown in FIG. 15B can be avoided by offsetting the edge of the sensor package 1 mm below the edge of the tooth, such that any movement in the occlusal direction will cause a drop in the proximity sensor output. All mouthguards used in subsequent in vivo experiments are constructed with 2 mm material thickness and 1 mm offset in sensor position.

After unit-testing the sensor components, a full mouthguard is built to characterize its in vivo sensing behavior and to determine an appropriate on-teeth and off-teeth threshold. A human subject performs a range of on-teeth and off-teeth events with the mouthguard. On-teeth events performed include talking, shouting, biting, and chewing. Off-teeth events performed include mouthguard manual manipulation, dropping, and helmet insertion. Proximity sensor readings from on-teeth events and off-teeth events are each fitted to a normal distribution. From these distributions, a proximity sensor threshold is chosen to maximize the likelihood of detecting all on-teeth events while rejecting all off-teeth events.

The chosen on-teeth and off-teeth proximity threshold is verified by measuring the corresponding amount of in vivo mouthguard dislocation. In one experiment, a human subject puts on and takes off a mouthguard while the mouthguard movement is tracked using an Ascension 3-D guidance trak-STAR system (Ascension Technology Corporation, Shelburne, Vt.), where two small 6 degree-of-freedom electromagnetic sensors are used, one fixed on the mouthguard and the other on the subject's head. The change in distance between these two sensors is tracked and recorded as the mouthguard dislocation distance. Proximity sensor readings are obtained continuously during the mouthguard movement and time-synchronized with the tracked distance. To control for errors, the experiment is conducted in a metal-free environment, and the Ascension system is characterized to have an offset error of approximately 1 mm in the measurement range, which is accounted for in all distance measurements.

Figure 16A:
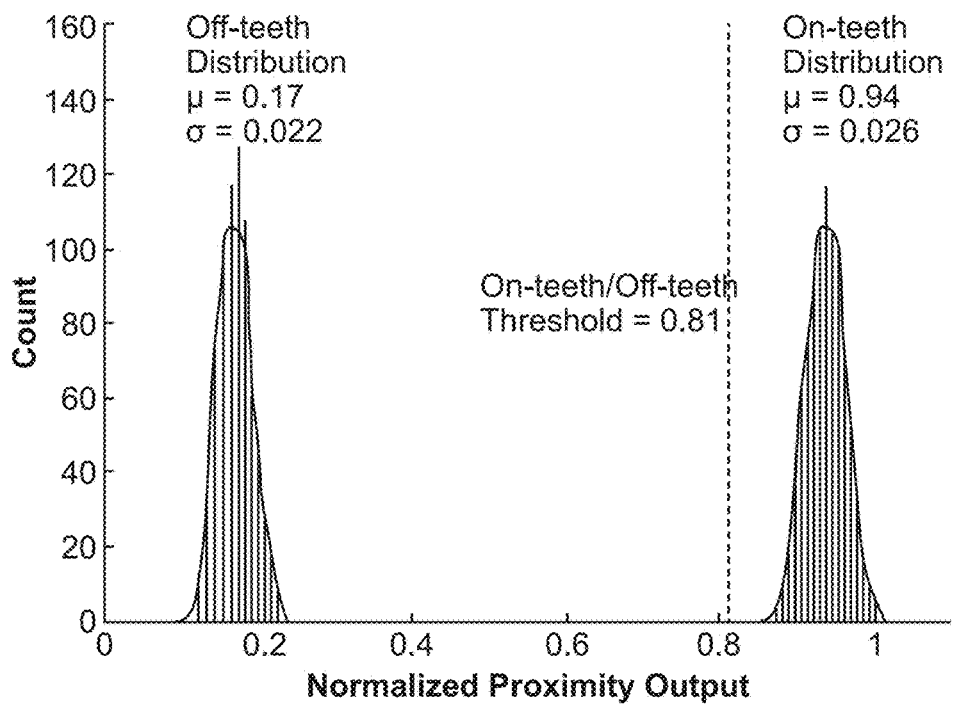
FIG. 16A and FIG. 16B illustrate the distribution of in vivo experimental results of an infrared proximity sensor and the determination of an on-teeth and off-teeth threshold.
Figure 16B:
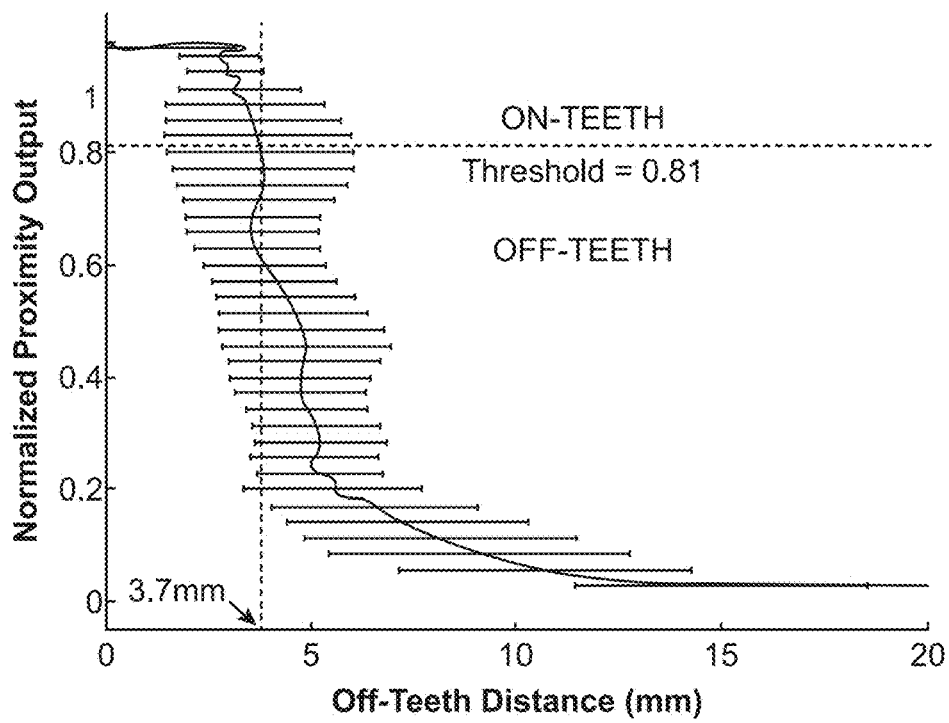

FIG. 16A and FIG. 16B illustrate the determination and verification of the on-teeth and off-teeth threshold of the proximity sensor using in vivo measurement results. On-teeth and off-teeth proximity sensor output distributions are shown in FIG. 16A. A threshold at 5 standard deviations below the on-teeth mean (a normalized proximity value of 0.81) is chosen, which corresponds to a probability of misclassifying 1 in every 3 million on-teeth events as an off-teeth event. This threshold is also 29 standard deviations above the off-teeth mean, which maximizes the rejection of off-teeth events as well. In addition, a majority of events that may have proximity sensor outputs between the on-teeth and off-teeth distributions, such as transitional events during which the mouthguard is put on or taken off the teeth, can be rejected. The average in vivo mouthguard off-teeth distance corresponding to the chosen threshold is 3.7 mm±2.2 mm of standard deviation as shown in FIG. 16B. The standard deviation may have resulted from slightly different 3-D mouthguard trajectories in each trial. Considering that maxillary (upper) teeth are 5 to 10 mm long, this off-teeth distance is less than a tooth length.

3. SVM Classifier Trained to Reject Non-Impact Events

A SVM method in this example is a statistical pattern recognition method that is effective at recognizing human motions. A SVM classifier can be trained with frequency domain features of linear and rotational motions to distinguish between impacts and non-impact events.

To train the SVM classifier and evaluate the overall device performance, a labeled data set including both head impacts and non-impact events simulating field conditions is obtained. Head impacts are reconstructed using a spring-driven impactor and a dummy head-form. Impacts at 5 different orientations and 8 velocities ranging from 2.1 to 8.5 meter-per-second (m/s) as listed in Table 2 are reconstructed. An instrumented mouthguard firmly clamped on the upper jaw of the head-form records the reconstructed head impacts. For non-impact reconstruction, videos of multiple football practices and games are observed to identify a comprehensive set of non-impact sources. Two subjects then wear the instrumented mouthguards and simulate all types of non-impact events.

Figure 17A:
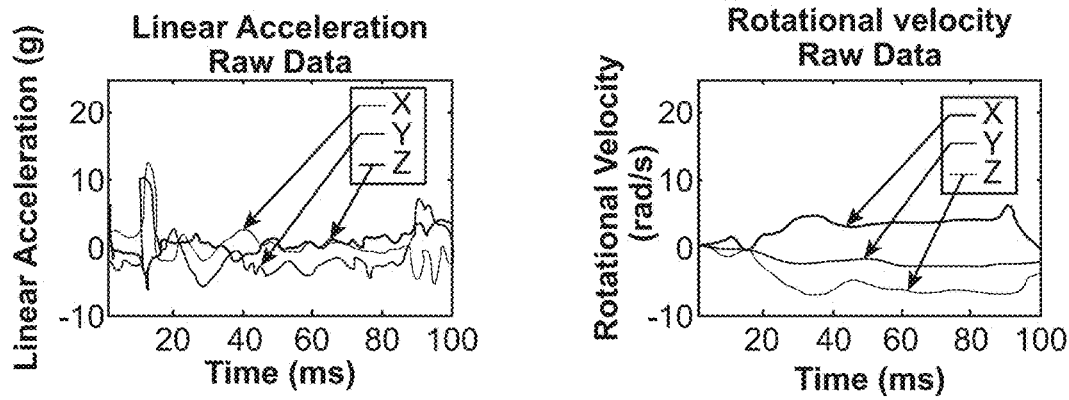
FIG. 17A, FIG. 17B, and FIG. 17C illustrate a motion data processing method.

The lab-reconstructed events are partitioned into a training portion for training the SVM classifier, and a testing portion to evaluate the overall system performance. Raw data collected include linear accelerations and rotational velocities in x, y, and z axes. From these data, frequency domain features rather than time domain features are extracted because impacts and non-impact events are expected to involve differences in orders-of-magnitude in colliding masses and therefore different dynamics. Power spectral density (PSD) features are computed from the raw motion data as shown in FIG. 17A. PSD magnitudes of the collected data are calculated between 15 Hz and 400 Hz. 15 Hz is the minimum frequency chosen due to a limited time window for data sampling, and 400 Hz is the maximum frequency because it is below the Nyquist frequency for all raw data vectors. The accelerometer chip used has a bandwidth of 500 Hz, which encompasses the full PSD range. The bandwidth of the gyroscope chip used is 184 Hz for the chosen sampling rate, and PSD above this frequency is discarded.

TABLE 2

Types and Numbers of Lab-Reconstructed Events

| Event Class | Description | Number Simulated | Event Number |
|---|---|---|---|
| Head Impact | Front | 16 | — |
| | Front Boss | 32 | — |
| | Rear Boss | 32 | — |
| | Rear | 32 | — |
| | Front Face Guard | 16 | — |
| Total | | 128 | |
| Spurious Non-impact Event | Manual manipulation (out-of-mouth) or striking mouthguard against object | 84 | 1-84 |
| | Off-teeth biting or chewing | 169 | 85-253 |
| | Dropping mouthguard on the ground | 136 | 254-389 |
| | Inserting mouthguard into helmet | 136 | 390-525 |
| | Putting on/taking off mouthguard | 84 | 526-609 |
| | On-teeth biting or chewing | 89 | 610-698 |
| | Shouting, talking, suction | 72 | 699-770 |
| Total | | 770 | |

Figure 17B:
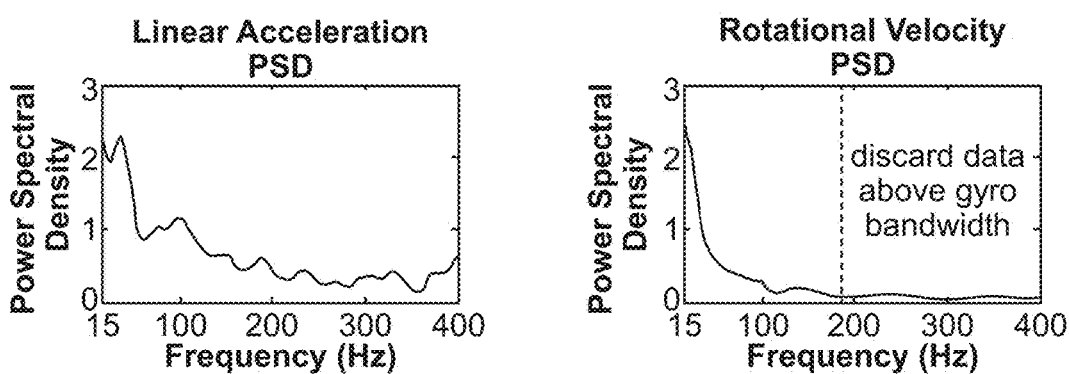
Figure 17C:
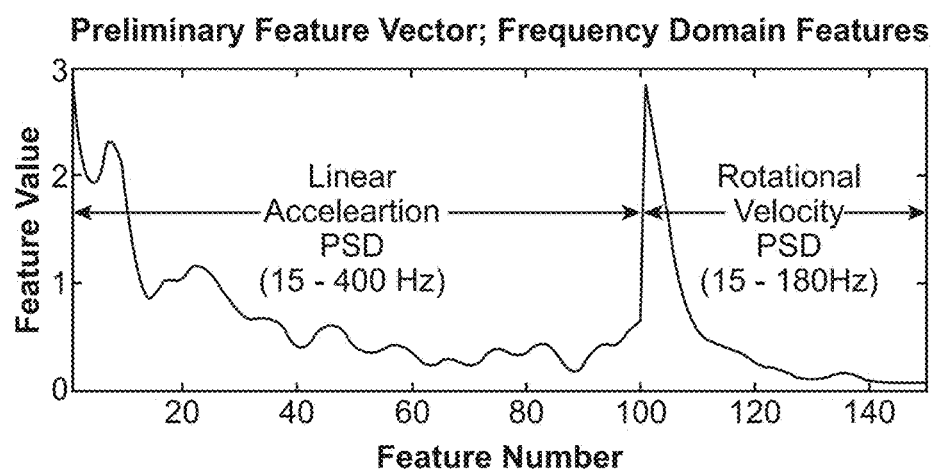

All PSD information can be combined into a single preliminary feature vector for SVM training. The PSD vectors in x, y, and z axes are interpolated into a common frequency vector due to different sampling rates in different chips. In this example, as illustrated in FIG. 17B, the common frequency vector contains 100 frequencies evenly spaced between 15 and 400 Hz for linear acceleration PSD and 50 frequencies evenly spaced between 15 and 180 Hz for rotational velocity PSD. PSD magnitudes are then concatenated into a 150-element preliminary feature vector containing both linear acceleration and rotational velocity PSD magnitude vectors for each event as shown in FIG. 17C.

From the preliminary feature vector, a subset of features that optimizes classifier performance is chosen. First, features are selected to minimize misclassification of events in the training data. To avoid bias, feature selection is performed using information from the training data only. Pearson correlation coefficients between all 150 features in the preliminary feature vector and the class labels (impact or non-impact) are calculated for events in the training data. Features are selected in a sequential process, starting with those that have high correlations to the class labels but low correlations to other already selected features. This selected subset of features can be used to train a SVM classifier with a radial basis function kernel. In order to find the best SVM decision boundary, a "pattern search" function in Matlab optimization toolbox can be used to minimize the misclassification rate within the training data. A decision boundary is chosen to have a sensitivity of greater than 95% and to maximize F-measure, namely the harmonic mean of the sensitivity and the precision.

Figure 18A:
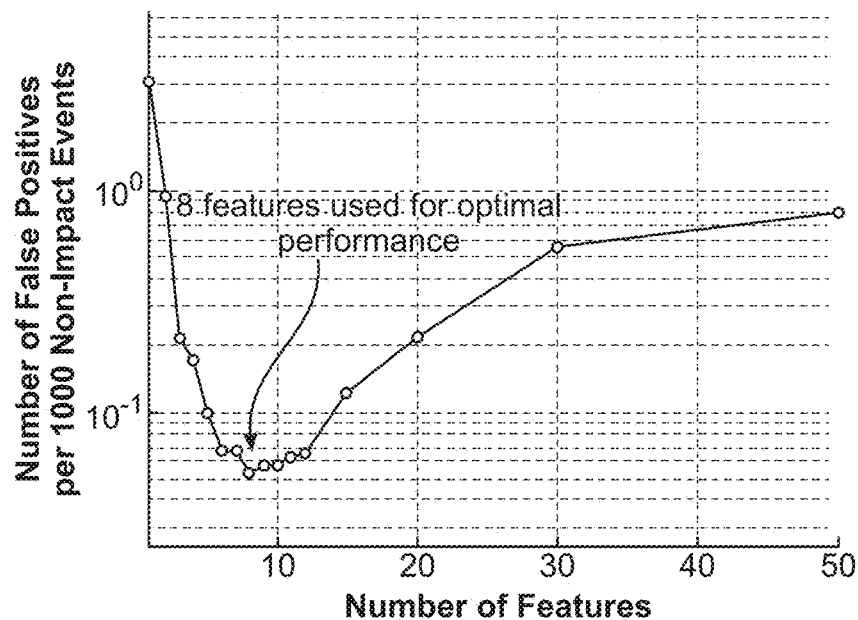
FIG. 18A and FIG. 18B illustrate results of SVM feature selection for optimal classification performance.
Figure 18B:
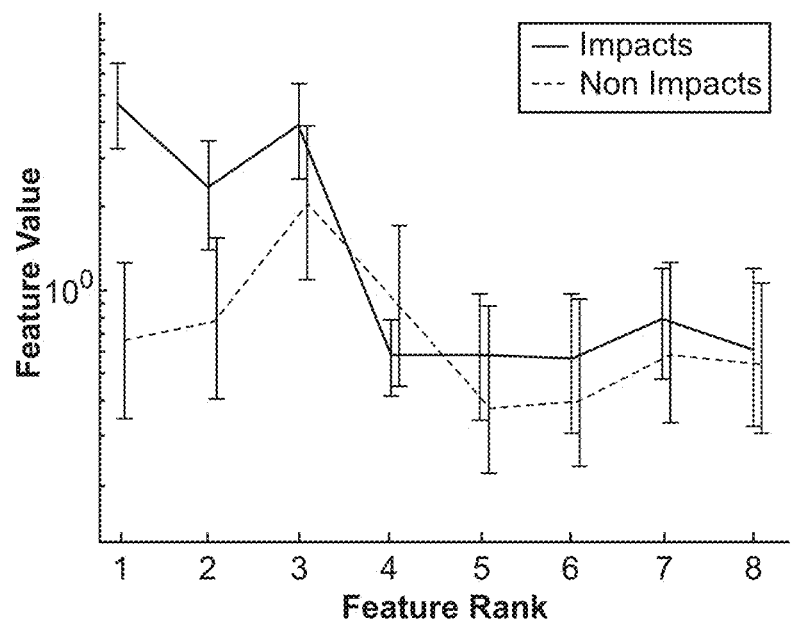

Features selected using the sequential feature selection process are ranked, with top features having high correlations to the class labels and low correlations to one another. The optimal number of features is chosen by monitoring classification performance while varying the number of features used as shown in FIG. 18A. An optimal set of 8 features as shown in Table 3 is chosen to minimize false positive rate in this example, even though anywhere from 6 to 11 features produce nearly the same result. Selected feature values have log-normal distributions, and their medians and interquartile ranges (IQRs) are shown in Table 3. The highest ranked features have very different values between impacts and non-impact events, while lower ranked features have more overlap between impacts and non-impact events as shown in FIG. 18B. On average, impacts have much higher linear acceleration PSD magnitudes at low frequencies (e.g., features 1 and 2) than non-impact events, with very little overlap between the interquartile ranges. Similar trends are observed in rotational velocity features at low frequencies (e.g., features 3 and 4). Although there is very little difference between the linear acceleration PSD magnitudes of impacts and non-impact events at high frequencies (e.g., features 5 to 8), the slight difference in feature values further helps to distinguish between the two types of events.

TABLE 3

Optimal Feature Set for Classification

| Data Type | Frequency (Hz) | Feature Rank | Median Value, Impacts (IQR) | Median Value, Non-Impact Events (IQR) |
|---|---|---|---|---|
| Linear Acceleration | 15 | 1 | 4.75 (3.15) | .67 (.91) |
| | 50 | 2 | 2.33 (2.00) | .78 (1.10) |
| | 132 | 7 | .79 (.69) | .58 (.90) |
| | 190 | 8 | .61 (83) | .50 (.76) |
| | 302 | 6 | .57 (.67) | .40 (.69) |
| | 345 | 5 | .58 (.61) | .37 (.65) |
| Rotational Velocity | 15 | 3 | 3.95 (2.90) | 2.11 (2.76) |
| | 58 | 4 | .58 (.34) | .85 (1.19) |

4. Device Performance

The performance of the event classification device in this example is evaluated on a testing portion of the lab-reconstructed data. To measure the device performance, the event classification device is used to classify events in the testing data as either impacts or non-impact events, and the classification results are compared to a priori labeled data set information. First, events in the testing data with proximity sensor readings below the on-teeth and off-teeth threshold are rejected as off-teeth, non-impact events, while events with proximity sensor readings above the threshold remain unclassified as potential impacts. The same features used for SVM training are then extracted from the unclassified events to classify the events using the SVM decision boundary determined during training. After the classification, numbers of true positives (TP), false positives (FP), true negatives (TN), and false negatives (FN) are calculated. Sensitivity, precision, specificity, and accuracy are calculated as classification performance measures, which are defined as:

$$\text{sensitivity} = \frac{TP}{TP + FN}; \quad (1)$$

$$\text{precision} = \frac{TP}{TP + FP}; \quad (2)$$

$$\text{specificity} = \frac{TN}{TN + FP}; \quad (3)$$

and $$\text{accuracy} = \frac{TP + TN}{TP + FP + TN + FN}. \quad (\$)$$

The main measures used to evaluate device performance are sensitivity and precision. Sensitivity is important because an impact detection device should not reject valid head impact events. Precision is also an important measure of device performance because it is not desirable to classify non-impact events as impacts and report a large number of false positives. Typically, precision is preferred over specificity as a performance measure because a large number of true negatives are expected on the field, which can give high specificity even with a substantial amount of false positives according to equation (3). Furthermore, since sensitivity and precision vary based on decision threshold, the area under the receiver operating characteristic (ROC) curve is also used as a measure of the performance of the classifier.

Because of variability in data partitioning, 100 Monte Carlo simulations of 5-fold cross-validation are conducted to obtain an unbiased estimate of the classification device's average performance. At the beginning of each cross-validation cycle, all impacts and non-impact events are randomly partitioned into 5 approximately equal portions. For each pass of the cross-validation, four portions are used to perform feature selection and SVM classifier training, and the remaining portion is used to evaluate the performance of the classification device. The sensitivity, precision, specificity, accuracy, and area under the ROC curve are recorded for each pass of the cross-validation and averaged at the end of all simulations to estimate the true performance of the classification device.

To compare the classification methods disclosed in this example with linear acceleration thresholding method and to verify the effectiveness of each classification subsystem, performances of four classification methods are evaluated:
1) Peak linear acceleration thresholding, where all events with peak linear acceleration magnitude greater than a predetermined threshold (e.g., 10 g) are classified as impacts;
2) Peak linear acceleration thresholding (e.g., 10 g) with a proximity classification subsystem to show the value of the proximity sensing;
3) Classification using only a SVM classifier to demonstrate its stand-alone performance; and
4) Combined SVM and proximity classification to show the overall device performance.

As shown in the laboratory evaluation results in Table 4, 10 g linear acceleration thresholding gives a sensitivity of 92%, with poor precision (37%), specificity (58%), and accuracy (65%), because a large number of non-impact events are misclassified as impacts. Adding infrared proximity classification to linear acceleration thresholding results in substantially improved performance: the sensitivity remains the same (92%), but the precision is much higher (92%) because this method could reject off-teeth, non-impact events. SVM classification alone also performs much better than the 10 g linear acceleration thresholding method, at a sensitivity of 98% and a precision of 97%. Combining SVM classification with proximity classification improves the classification performance to a sensitivity of 98% and a precision of 99.98%. If the sensitivity is lowered to 96%, no non-impact events are misclassified.

TABLE 4

Evaluation of Head Impact Classification System

|  | 10 g Threshold only | 10 g Threshold + Proximity | SVM Alone | SVM + Proximity |
|---|---|---|---|---|
| Sensitivity | .92 | .92 | .98 | .98 |
| Precision | .37 | .92 | .97 | .9998 |
| Specificity | .58 | .96 | .99 | .9999 |

TABLE 4-continued

Evaluation of Head Impact Classification System

|  | 10 g Threshold only | 10 g Threshold + Proximity | SVM Alone | SVM + Proximity |
|---|---|---|---|---|
| Accuracy | .65 | .94 | .99 | .99 |
| Area Under ROC | .780 (.031) | .979 (.005) | .998 (.001) | 1 (.000) |

Figure 19:
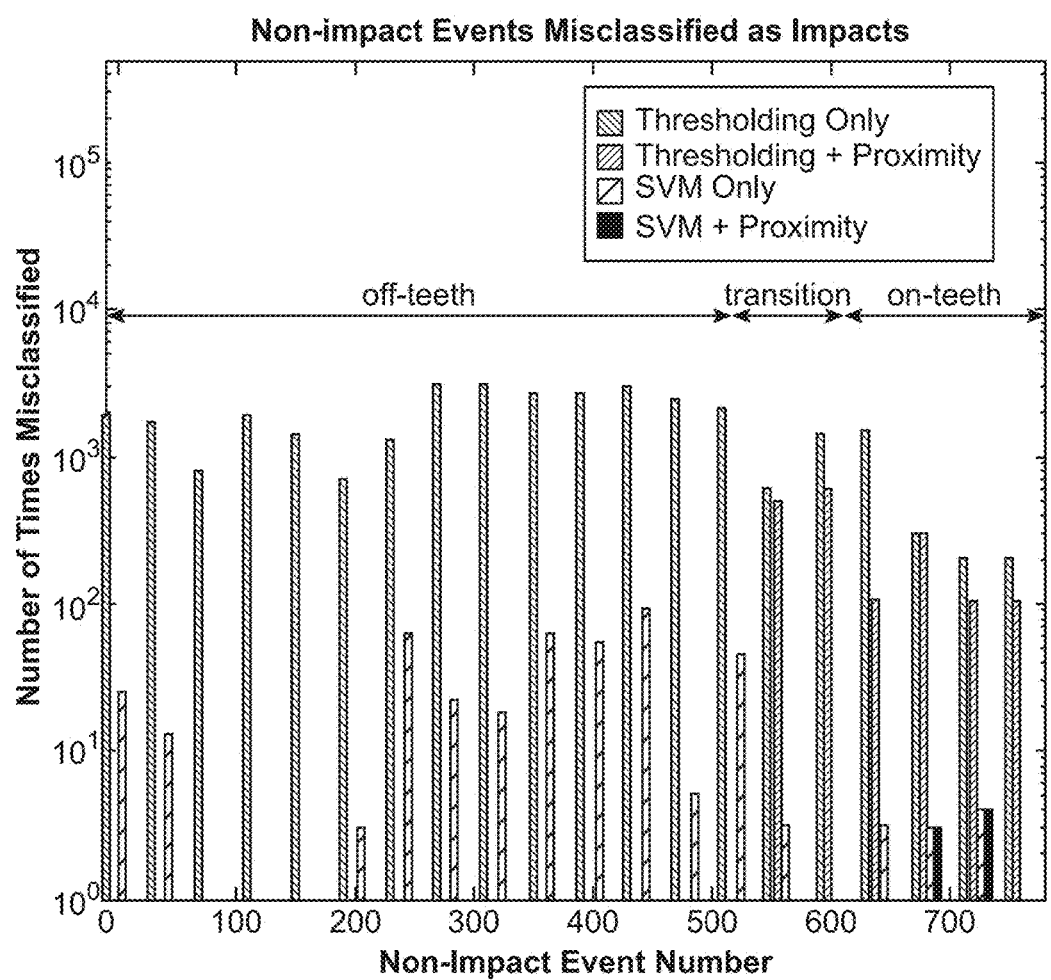
FIG. 19 illustrates distributions of misclassified events using a motion event classifier and different classification methods.

A distribution of misclassified events pooled over the 100 Monte Carlo simulations is illustrated in FIG. 19. Linear acceleration thresholding method has more misclassifications than other methods, with false positives relatively evenly distributed across all types of non-impact events. The proximity classification subsystem successfully rejects all off-teeth, non-impact events. But this subsystem is not designed to recognize on-teeth, non-impact event. It also has trouble with some transitional events because proximity sensor output is sampled once for each event, which does not capture the full duration of the event. Adding a SVM subsystem helps to reject a majority of the on-teeth, non-impact events and transitional events. In fact, the SVM classifier has good stand-alone performance that is much improved over the linear acceleration thresholding method as shown in Table 4. However, the SVM classifier alone misclassifies off-teeth events such as inserting the mouthguard into a helmet or dropping the mouthguard. Therefore, combining the two classification subsystems maximizes the rejection of non-impact events by allowing the strength of each subsystem to overcome the weakness of the other. The combined system misclassifies a few high-acceleration on-teeth biting and chewing events as shown in FIG. 19.

An embodiment of the disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the invention, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

While certain conditions and criteria are specified herein, it should be understood that these conditions and criteria apply to some embodiments of the disclosure, and that these conditions and criteria can be relaxed or otherwise modified for other embodiments of the disclosure.

While the invention has been described with reference to the specific embodiments thereof, it should be understood by those skilled in the art that various changes may be made and equivalents may be substituted without departing from the true spirit and scope of the invention as defined by the appended claim(s). In addition, many modifications may be made to adapt a particular situation, material, composition of matter, method, operation or operations, to the objective, spirit and scope of the invention. All such modifications are intended to be within the scope of the claim(s) appended hereto. In particular, while certain methods may have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

The invention claimed is:

1. An oral appliance comprising:
a base member having a generally U-shaped form defining a channel to receive a row of teeth of a human subject;
an emitter affixed to the base member, wherein the emitter is configured to emit a wave signal;
a receiver affixed to the base member, wherein the receiver is positioned relative to the emitter such that the receiver is configured to detect a reflected wave signal originating from the emitter when the base member is placed on the row of teeth;
a motion sensor affixed to the base member;
a processor in electronic communication with the receiver and the motion sensor; and
a memory in electronic communication with the processor, wherein the memory comprises program code which, when executed by the processor, configures the processor to:
detect an event from data received from the motion sensor based on a determination that the data received from the motion sensor is indicative of motion exceeding a kinematic threshold;
responsive to a detection of the event from the data received from the motion sensor, determine from data received from the receiver whether the base member is properly engaged on the teeth;
in the case in which the base member is determined to not be properly engaged on the teeth, reject the event indicated by the data received from the motion sensor as being a non-impact event, and
in the case in which the base member is determined to be properly engaged on the teeth, determine from the data received from the motion sensor that an on-body event has occurred, and classify the on-body event as a head impact based on frequency domain features of the data from the motion sensor.

2. The oral appliance of claim 1, further comprising a light sensor affixed to the base member and configured to detect ambient light.

3. The oral appliance of claim 1, wherein the program code comprises code to direct the processor to process data received from the receiver and the motion sensor using a machine learning technique to identify a head collision.

4. The oral appliance of claim 3, wherein the machine learning technique is a support vector machine classifier.

5. The oral appliance of claim 1, wherein the program code comprises code to direct the processor to, responsive to the detection of the event from the data received from the motion sensor, obtaining the data from the receiver to determine whether the base member is properly engaged on the teeth.

6. A device for motion event classification, comprising:
a base member;
an engagement sensor affixed to the base member;
a motion sensor affixed to the base member;
a processor in electronic communication with the engagement sensor and the motion sensor; and
a memory in electronic communication with the processor, wherein the memory comprises program code which, when executed by the processor, configures the processor to:
detect a first event from data received from the motion sensor based on a determination that the data received from the motion sensor during the first event is indicative of motion exceeding a kinematic threshold;
responsive to a detection of the first event, determine from data from the engagement sensor whether the base member is properly engaged or not properly engaged during the first event;
classify the first event as an on-body event based on a determination that the base member is properly engaged during the first event, and based on frequency domain features of the data received from the motion sensor during the first event;
detect a second event from data received from the motion sensor based on a determination that the data received from the motion sensor during the second event is indicative of motion exceeding the kinematic threshold;
responsive to a detection of the second event, determine from data from the engagement sensor whether the base member is properly engaged or not properly engaged during the second event; and
classify the second event as a non-impact event based on a determination that the base member is not properly engaged during the second event.

7. The device of claim 6, wherein the base member comprises one of a mouthguard, a tooth patch, an ear plug, a body patch, and a nose patch.

8. The device of claim 6, wherein the engagement sensor comprises a proximity sensor, and the proximity sensor comprises a pre-stressed strain sensor.

9. The device of claim 6, wherein the engagement sensor comprises a proximity sensor, and the proximity sensor comprises a pulse oximeter.

10. The device of claim 6, wherein the engagement sensor comprises an ultrasonic proximity sensor comprising an emitter and receiver pair.

11. The device of claim 6, further comprising a light sensor affixed to the base member and configured to detect ambient light.

12. The device of claim 6, further comprising an alert generator for indicating the first event.

13. The device of claim 6, wherein the program code comprises code to direct the processor to process the data received from the engagement sensor and the motion sensor during the first event to classify the first event.

14. The device of claim 13, wherein the program code comprises code to direct the processor to classify the first event as the on-body event based on a detection of a placement of the base member on a human subject during the first event.

15. The device of claim 13, wherein the program code comprises machine learning code to classify the first event.

16. The device of claim 15, wherein the machine learning code is a support vector machine classifier.

17. The device of claim 6, wherein the program code comprises code to direct the processor to, responsive to the detection of the first event from the data received from the motion sensor during the first event, obtaining the data from the engagement sensor to determine whether the base member is properly engaged or not properly engaged during the first event.

18. A method of impact detection, comprising:
   receiving at a processor, from an impact detection device coupled to the processor, placement data of the impact detection device relative to a human body during an event and motion data of the impact detection device during the event;
   the processor classifying the event as one of either an on-body, impact event or a non-impact event based on a combination of the placement data and the motion data, and further classifying the on-body impact event based on frequency domain features of the motion data;
   wherein classifying the event comprises:
      detecting the event from the motion data by determining that the motion data exceeds a kinematic threshold;
      responsive to detecting the event, determining from the placement data whether the impact detection device is properly engaged; and
      rejecting the motion data related to the event when it is determined that the impact detection device is not properly engaged.

19. The method of claim 18, wherein classifying the event as the on-body, impact event is based on the placement data indicating that the impact detection device is properly engaged on the human body.

20. The method of claim 18, wherein classifying the event as the on-body, impact event is based on a machine learning technique.

21. The method of claim 18, wherein classifying the event as the on-body, impact event comprises computing the frequency domain features from the motion data, and applying a machine learning technique to the frequency domain features to recognize the event as the on-body, impact event.

22. The method of claim 21, wherein applying the machine learning technique to the frequency domain features comprises determining a power spectral density of head motion data for each frequency of a set of frequencies between 15 Hz and 400 Hz, and creating a feature vector of power spectral densities, where each power spectral density of the feature vector corresponds to a frequency in the set of frequencies.

23. The method of claim 18, wherein classifying the event as the non-impact event comprises determining that the placement data indicates that the impact detection device is not fully engaged.

24. The method of claim 18, wherein the impact detection device is an oral appliance, and classifying the event as the on-body, impact event comprises determining that the oral appliance is in a position of full engagement.

25. The method of claim 18, further comprising receiving at the processor, from a microphone coupled to the processor, acoustic information corresponding to the event, wherein classifying the event as the on-body, impact event comprises classifying the acoustic information as a head impact.

* * * * *